US012296059B2

United States Patent
Imai

(10) Patent No.: US 12,296,059 B2
(45) Date of Patent: May 13, 2025

(54) ULTRAVIOLET LIGHT FLUID TREATMENT DEVICE

(71) Applicant: NICHIA CORPORATION, Anan (JP)

(72) Inventor: Masahiro Imai, Chino (JP)

(73) Assignee: Nichia Corporation, Anan (JP)

( * ) Notice: Subject to any disclaimer, the term of this patent is extended or adjusted under 35 U.S.C. 154(b) by 510 days.

(21) Appl. No.: 17/849,070

(22) Filed: Jun. 24, 2022

(65) Prior Publication Data
US 2023/0011539 A1    Jan. 12, 2023

(30) Foreign Application Priority Data

Jul. 8, 2021  (JP) .................................. 2021-113659
Sep. 17, 2021 (JP) .................................. 2021-152304
Dec. 10, 2021 (JP) .................................. 2021-201186

(51) Int. Cl.
*A61L 2/10* (2006.01)
*A61L 2/26* (2006.01)
*C02F 1/32* (2023.01)

(52) U.S. Cl.
CPC ........ *A61L 2/10* (2013.01); *A61L 2/26* (2013.01); *C02F 1/325* (2013.01); *A61L 2202/11* (2013.01); *C02F 2201/3227* (2013.01); *C02F 2303/04* (2013.01)

(58) Field of Classification Search
CPC .......... A61L 2/10; A61L 2/26; A61L 2202/11; C02F 1/325; C02F 2201/3227; C02F 2303/04
See application file for complete search history.

(56) References Cited

U.S. PATENT DOCUMENTS

| | | | |
|---|---|---|---|
| 7,270,748 B1* | 9/2007 | Lieggi ...................... | C02F 1/325 |
| | | | 250/435 |
| 2011/0114546 A1* | 5/2011 | Barsky .................... | C02F 1/325 |
| | | | 210/199 |
| 2012/0138545 A1* | 6/2012 | Soler ......................... | C02F 1/30 |
| | | | 422/186.3 |
| 2016/0052802 A1 | 2/2016 | Ochi et al. | |

(Continued)

FOREIGN PATENT DOCUMENTS

| | | |
|---|---|---|
| CN | 109250785 A | 1/2019 |
| CN | 109250786 A | 1/2019 |
| CN | 112499722 A | 3/2021 |

(Continued)

*Primary Examiner* — Sean M Luck
(74) *Attorney, Agent, or Firm* — Kim & Stewart LLP

(57) ABSTRACT

An ultraviolet light fluid treatment device includes an inlet, an outlet, a primary conduit, a secondary conduit, and a light source. The primary conduit connects the inlet and the outlet. The secondary conduit branches off the primary conduit at a first location of the primary conduit and merged with the primary conduit at a second location of the primary conduit. The light source is disposed between the primary conduit and the secondary conduit and configured to emit ultraviolet light, with which a region in the primary conduit is irradiated. A cross-sectional area in the primary conduit orthogonal to a first flow direction of a fluid in the primary conduit at the first location is greater than a cross-sectional area in the secondary conduit orthogonal to a second flow direction of the fluid in the secondary conduit at the first location.

20 Claims, 20 Drawing Sheets

(56) References Cited

U.S. PATENT DOCUMENTS

2016/0207795 A1     7/2016   Hanada
2018/0155215 A1*    6/2018   Torii ....................... C02F 1/325

FOREIGN PATENT DOCUMENTS

| | | |
|---|---|---|
| CN | 112551637 A | 3/2021 |
| JP | 2014-233646 A | 12/2014 |
| JP | 2015-174026 A | 10/2015 |
| JP | 2018-140001 A | 9/2018 |
| JP | 2018-161247 A | 10/2018 |
| JP | 2019-076643 A | 5/2019 |
| WO | 2014/192913 A1 | 12/2014 |
| WO | 2015/046014 A1 | 4/2015 |
| WO | 2019/049702 A1 | 3/2019 |

* cited by examiner

ULTRAVIOLET LIGHT FLUID TREATMENT DEVICE

CROSS-REFERENCE TO RELATED APPLICATION

This application claims priority to Japanese Patent Application No. 2021-113659 filed on Jul. 8, 2021, Japanese Patent Application No. 2021-152304 filed on Sep. 17, 2021, and Japanese Patent Application No. 2021-201186 filed on Dec. 10, 2021, the disclosures of which are hereby incorporated by reference in their entireties.

The present disclosure relates to an ultraviolet light fluid treatment device.

Japanese Patent Publication No. 2018-161247 discloses a device that irradiates a flow path of a fluid with ultraviolet light emitted by a light-emitting element.

SUMMARY

An object of the present disclosure is to provide an ultraviolet light fluid treatment device in which a light source can be cooled by a fluid treated by ultraviolet light from the light source while pressure loss of the fluid is suppressed.

According to an aspect of the present disclosure, an ultraviolet light fluid treatment device includes an inlet, an outlet, a primary conduit, a secondary conduit, and a light source. The primary conduit connects the inlet and the outlet. The secondary conduit branches off the primary conduit at a first location of the primary conduit and merged with the primary conduit at a second location of the primary conduit. The light source is disposed between the primary conduit and the secondary conduit and configured to emit ultraviolet light, with which a region in the primary conduit is irradiated. A cross-sectional area in the primary conduit orthogonal to a first flow direction of a fluid in the primary conduit at the first location is greater than a cross-sectional area in the secondary conduit orthogonal to a second flow direction of the fluid in the secondary conduit at the first location.

According to the present disclosure, it is possible to provide an ultraviolet light fluid treatment device in which a light source can be cooled by a fluid treated by ultraviolet light from the light source while pressure loss of the fluid is suppressed.

DESCRIPTION OF EMBODIMENTS

Figure 1:
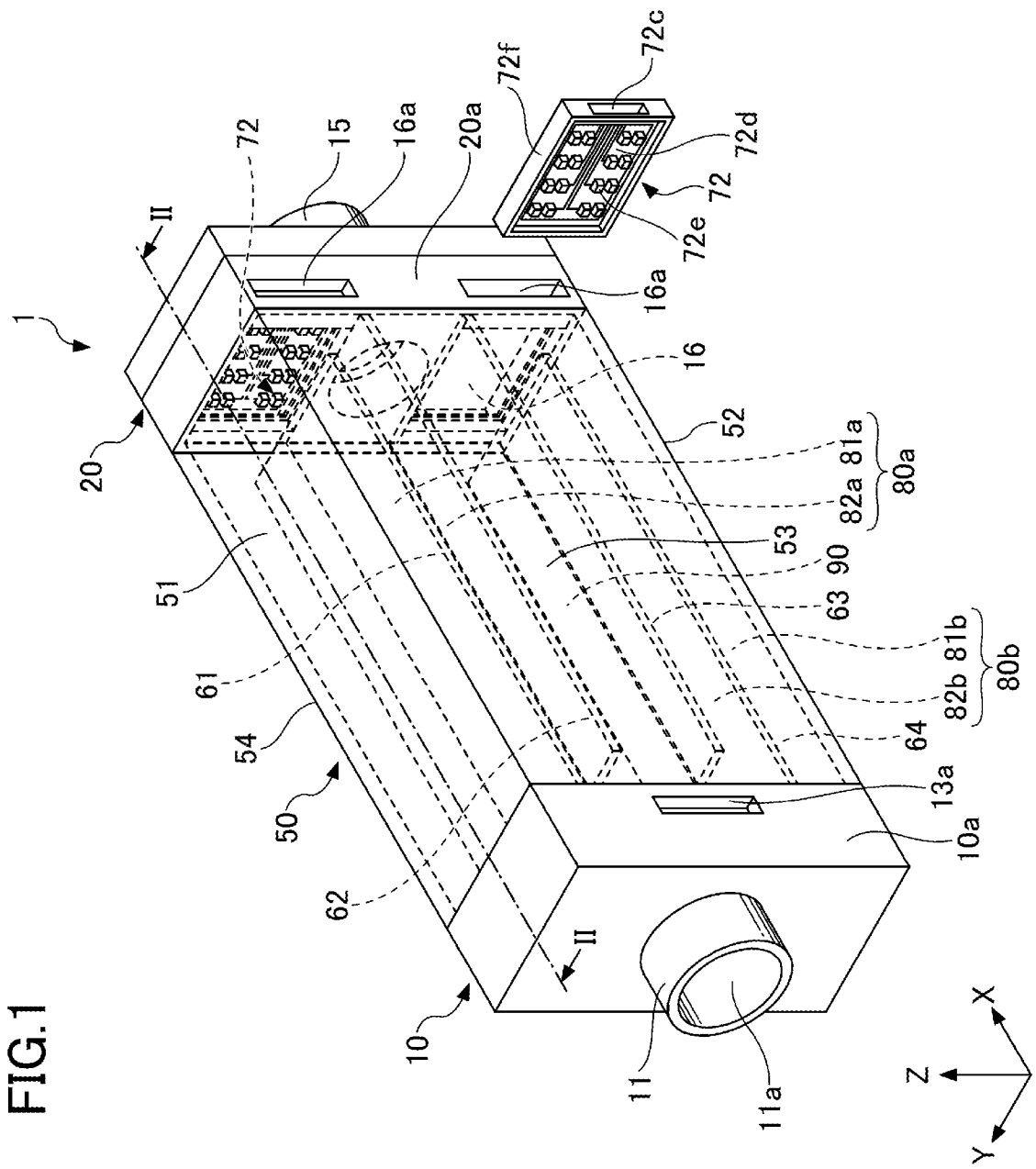
FIG. 1 schematically illustrates a perspective view of an ultraviolet light fluid treatment device according to an embodiment.

Embodiments will be described below with reference to the drawings. In the drawings, the same constituent elements are denoted using the same reference signs. It is noted that the drawings schematically illustrate embodiments, and thus scales and intervals of members, positional relationships, and the like may be exaggerated, or some of the members may not be illustrated in the drawings.

Figure 2:
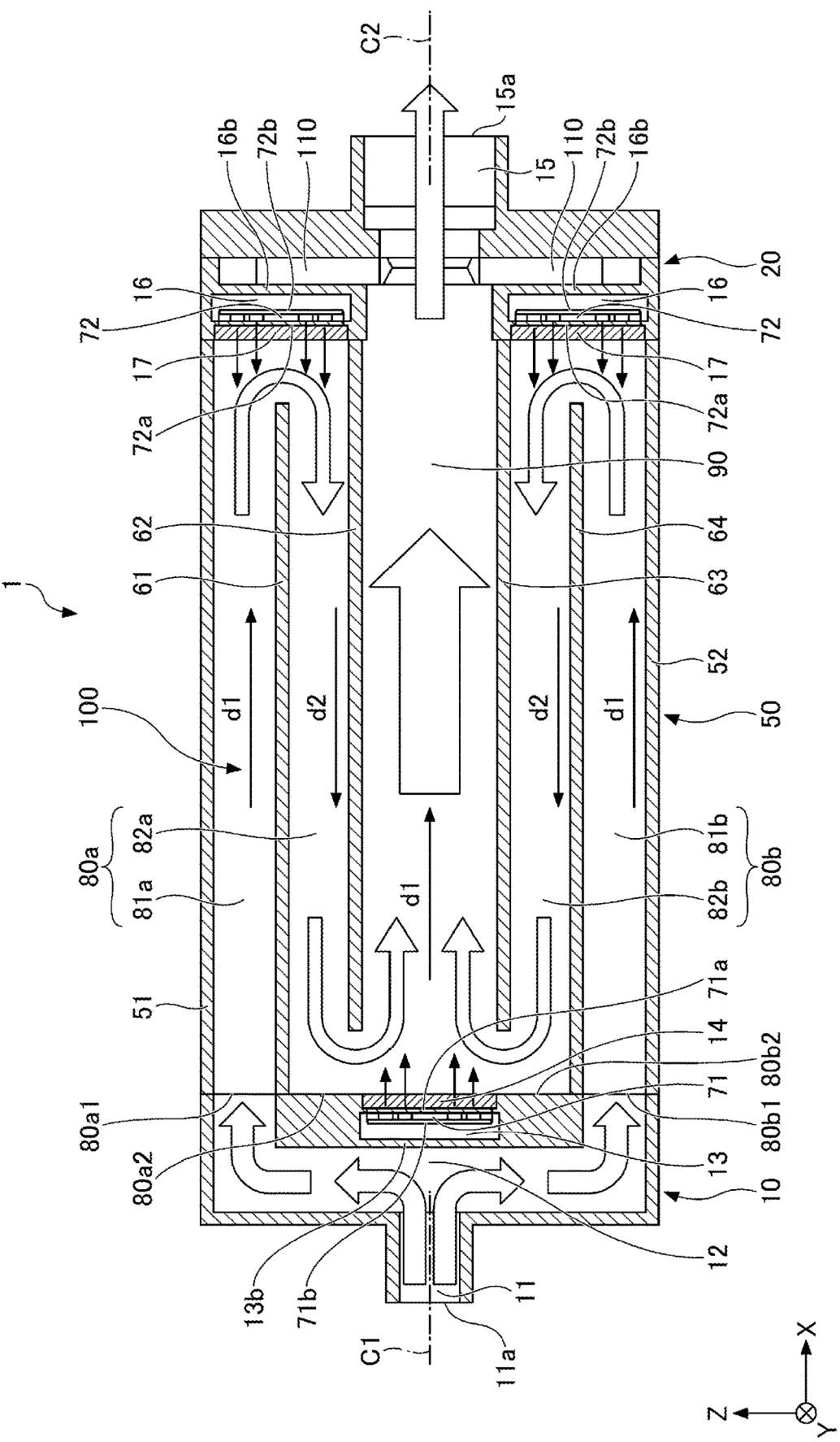
FIG. 2 schematically illustrates a cross-sectional view of the ultraviolet light fluid treatment device taken along line II-II in FIG. 1.

FIG. 1 schematically illustrates a perspective view of an ultraviolet light fluid treatment device 1 according to an embodiment of the present disclosure. FIG. 2 schematically illustrates a cross-sectional view of the ultraviolet light fluid treatment device 1 taken along line II-II in FIG. 1. In FIGS. 1 and 2, the three axes orthogonal to each other are denoted as an X axis, a Y axis, and a Z axis. The cross section illustrated in FIG. 2 is a cross section parallel to the X axis and the Z axis, and orthogonal to the Y axis.

The ultraviolet light fluid treatment device 1 includes a first end portion 10, a second end portion 20, and an intermediate portion 50 positioned between the first end portion 10 and the second end portion 20. Further, the ultraviolet light fluid treatment device 1 includes a first light source 71 and a second light source 72. In the example illustrated in FIGS. 1 and 2, the first light source 71 is disposed in the first end portion 10, and the second light source 72 is disposed in the second end portion 20.

The material of the first end portion 10, the second end portion 20, and the intermediate portion 50 is a metal such as stainless steel, for example. The first end portion 10, the second end portion 20, and the intermediate portion 50 may be separately configured from each other, or may be integrally configured.

In FIG. 2, a flow of fluid is indicated by bold arrows. Fluid such as a liquid or a gas flows from outside of the ultraviolet light fluid treatment device 1 into the first end portion 10. Further, the fluid flows from the first end portion 10 to the second end portion 20 via the intermediate portion 50, and then flows out of the second end portion 20 to the outside of the ultraviolet light fluid treatment device 1.

The first end portion 10 includes an inflow portion (may be referred to as an inlet) 11 for the fluid, an upstream flow path portion 12, a first light source placement portion 13, and a first window portion 14.

The inflow portion 11 includes a hole portion connecting the outside of the ultraviolet light fluid treatment device 1 with an interior of the first end portion 10. External piping is connected to the inflow portion 11, and the fluid flows into the inflow portion 11 from the piping. A shape of a cross section of the inflow portion 11 orthogonal to the direction of flow of the fluid is, for example, circular. The inflow portion 11 includes an inflow port 11a formed as a circular opening, for example. A central axis C1 passing through a center of the circular cross-sectional shape of the inflow portion 11 is parallel to an X-axis direction.

The upstream flow path portion 12 is connected to the inflow portion 11 in the interior of the first end portion 10. The upstream flow path portion 12 branches into a plurality of flow paths from the inflow portion 11. In the example illustrated in FIG. 2, the upstream flow path portion 12 branches into two from the inflow portion 11. For example, the upstream flow path portion 12 branches from the inflow portion 11 in directions opposite each other in a Z-axis direction orthogonal to the central axis C1.

The first light source placement portion 13 is formed as a space in the interior of the first end portion 10 in which the first light source 71 can be disposed. As illustrated in FIG. 1, a first opening 13a leading to the first light source placement portion 13 is formed in one lateral surface 10a of the first end portion 10. The first light source 71 can be detachably attached to the first light source placement portion 13 through this first opening 13a. The first light source placement portion 13 is formed as a space separated from each flow path portion of the ultraviolet light fluid treatment device 1, and the first light source 71 is not exposed to the fluid and is protected from the fluid. For example, in a case in which the fluid is a liquid, the first light source 71 does not require a liquid-proof structure. Further, the first light source 71 can be detached, replaced, and maintained while the fluid flows in the ultraviolet light fluid treatment device 1. It is noted that the first light source placement portion 13 may be formed in an interior of the intermediate portion 50. In this case, the first opening 13a leading to the first light source placement portion 13 is formed in a third wall portion 53 or a fourth wall portion 54 of the intermediate portion 50 described below.

The first light source 71 emits ultraviolet light. A peak wavelength of the ultraviolet light emitted by the first light source 71 is, for example, in a range from 10 nm to 400 nm. The first light source 71 includes one or more light-emitting elements. As the light-emitting element, a light-emitting diode (LED) or a laser diode (LD) can be used, for example. As the first light source 71, a device such as a light-emitting device obtained by mounting one or more light-emitting elements on a wiring substrate or the like, or a light-emitting device obtained by mounting a housing including one or more light-emitting elements on a wiring substrate or the like can be used. The first light source 71 includes a first surface 71a and a second surface 71b positioned on a side opposite to the first surface 71a. The first surface 71a is a light-outputting surface, and ultraviolet light is output from the first surface 71a.

The first window portion 14 faces the first surface 71a of the first light source 71. In the X-axis direction, the first surface 71a is positioned between the first window portion 14 and the second surface 71b of the first light source 71, and a portion of the upstream flow path portion 12 is positioned between the second surface 71b and the inflow portion 11. The first window portion 14 is formed of a material having transmissivity with respect to the wavelength of the ultraviolet light emitted by the first light source 71. Examples of the material of the first window portion 14 include inorganic materials formed of at least one type selected from the group consisting of quartz glass, borosilicate glass, calcium fluoride glass, aluminoborosilicate glass, oxynitride glass, chalcogenide glass, and sapphire.

The fluid flowing through the upstream flow path portion 12 of the first end portion 10 can cool the first light source 71 from the second surface 71b side. This makes it possible to suppress a decrease in light emission efficiency due to heat generation associated with the light emission of the first light source 71.

Figure 3:
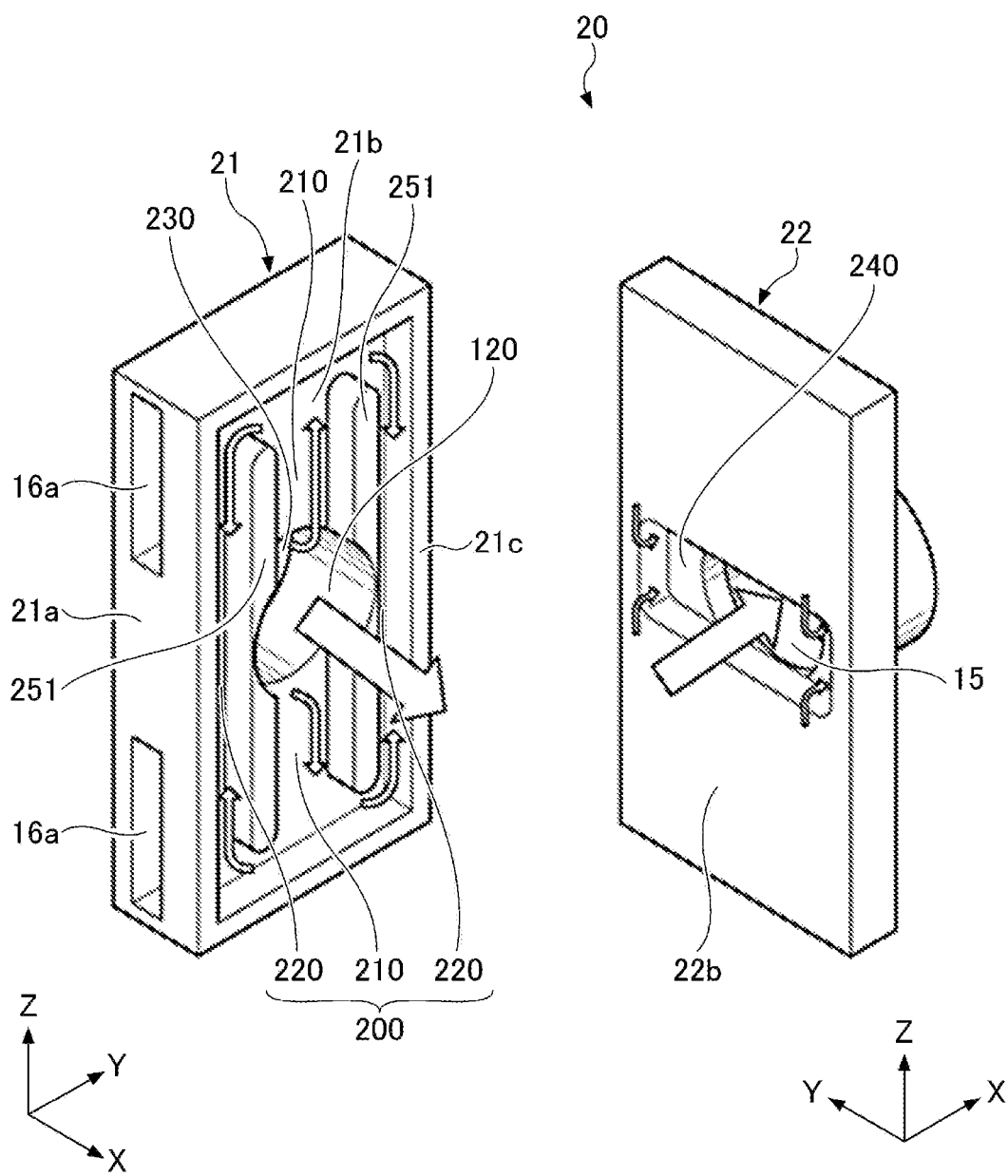
FIG. 3 illustrates an exploded perspective view of an example of a second end portion of the ultraviolet light fluid treatment device.

FIG. 3 illustrates an exploded perspective view of the second end portion 20.

The second end portion 20 includes an inner member 21 and an outer member 22. The inner member 21 is positioned between the intermediate portion 50 and the outer member 22 in the X-axis direction. The inner member 21 and the outer member 22 may be separately configured from each other or may be integrally configured.

The outer member 22 includes an outflow portion (may be referred to as an outlet) 15. The outflow portion 15 includes a hole portion that connects an interior of the second end portion 20 and the outside of the ultraviolet light fluid treatment device 1. External piping is connected to the outflow portion 15. The fluid flowing through an interior of the ultraviolet light fluid treatment device 1 flows out of the outflow portion 15 into the piping. A cross-sectional shape of the outflow portion 15 in a direction orthogonal to the direction of flow of the fluid is, for example, circular. The outflow portion 15 includes an outflow port 15a formed as a circular opening, for example.

A central axis C2 through a center of the circular cross-sectional shape of the outflow portion 15 coincides with the central axis C1 of the inflow portion 11. As a result, the ultraviolet light fluid treatment device 1 can be easily connected to the intermediate portion of straight piping that is generally available.

The inner member 21 includes a second light source placement portion 16. The second light source placement portion 16 is formed as a space in an interior of the inner member 21 in which the second light source 72 can be disposed. A plurality of the second light sources 72 are disposed in the interior of the inner member 21. In the present embodiment, for example, two second light sources 72 are disposed in the interior of the inner member 21. Accordingly, two second light source placement portions 16 are formed in the interior of the inner member 21. The two second light source placement portions 16 sandwich the outflow portion 15 in the Z-axis direction.

As illustrated in FIG. 1, a second opening 16a leading to the second light source placement portion 16 is formed in one lateral surface 21a of the inner member 21. The second light source 72 can be detachably attached to the second light source placement portion 16 through this second opening 16a. The second light source placement portion 16 is formed as a space separated from each flow path portion of the ultraviolet light fluid treatment device 1, and the second light source 72 is not exposed to the fluid and is protected from the fluid. For example, in a case in which the fluid is a liquid, the second light source 72 does not require a liquid-proof structure. Further, the second light source 72 can be detached, replaced, and maintained while the fluid flows in the ultraviolet light fluid treatment device 1. It is noted that the second light source placement portion 16 may be formed in the interior of the intermediate portion 50. In this case, the second opening 16a leading to the second light source placement portion 16 is formed in the third wall portion 53 or the fourth wall portion 54 of the intermediate portion 50 described below.

The second light source 72 emits ultraviolet light. As the second light source 72, the same light source as the first light source 71 can be used. As the second light source 72, a light source having an emission peak wavelength different from that of the first light source 71 may be used. The second light source 72 includes a first surface 72a and a second surface 72b positioned on a side opposite to the first surface 72a. The first surface 72a is a light-outputting surface, and ultraviolet light is output from the first surface 72a.

In the inner member 21, a second window portion 17 is disposed facing the first surface 72a of each second light source 72. The second window portion 17 is formed of a material having transmissivity with respect to the wavelength of the ultraviolet light emitted by the second light source 72. The second window portion 17 is formed of glass, for example. In the X-axis direction, the first surface 72a is positioned between the second window portion 17 and the second surface 72b of the second light source 72.

As illustrated in FIG. 1, the second light source 72 includes, for example, a wiring substrate 72d, a plurality of light-emitting elements 72e mounted on the wiring substrate 72d, and a housing 72f covering the wiring substrate 72d and the light-emitting elements 72e. An insertion port 72c of a connector electrically connected to the wiring substrate 72d is formed in the housing 72f. The first light source 71 can also be configured in the same or similar manner as the second light source 72. The first light source 71 and the second light source 72 may have a waterproof structure. In this case, the member having light transmissivity constituting the first window portion 14 and the second window portion 17 may be omitted, and ultraviolet light from the first light source 71 and the second light source 72 may be directly irradiated from the first light source placement portion 13 and the second light source placement portion 16 into flow path portions 80a, 80b, 90.

In the example illustrated in FIG. 1, the intermediate portion 50 includes four wall portions (i.e., a first wall portion 51, a second wall portion 52, the third wall portion 53, and the fourth wall portion 54) constituting the housing of the intermediate portion 50. The first wall portion 51 and the second wall portion 52 are separated from each other in the Z-axis direction. The third wall portion 53 and the fourth wall portion 54 are separated from each other in a Y-axis direction.

Furthermore, the intermediate portion 50 includes a plurality of partition members 61 to 64 disposed in a space surrounded by the first wall portion 51, the second wall portion 52, the third wall portion 53, and the fourth wall portion 54. For example, the four partition members (i.e., a first partition member 61, a second partition member 62, a third partition member 63, and a fourth partition member 64) are disposed in the intermediate portion 50.

The first partition member 61, the second partition member 62, the third partition member 63, and the fourth partition member 64 are each a plate member having a rectangular shape elongated in the X-axis direction. The first wall portion 51, the first partition member 61, the second partition member 62, the third partition member 63, the fourth partition member 64, and the second wall portion 52 are separated from one another in the Z-axis direction.

In the Z-axis direction, the first partition member 61 is positioned between the first wall portion 51 and the second partition member 62, the second partition member 62 is positioned between the first partition member 61 and the third partition member 63, the third partition member 63 is positioned between the second partition member 62 and the fourth partition member 64, and the fourth partition member 64 is positioned between the third partition member 63 and the second wall portion 52.

The first partition member 61, the second partition member 62, the third partition member 63, and the fourth partition member 64 are interposed between the third wall portion 53 and the fourth wall portion 54 in the Y-axis direction. Both end portions in the Y-axis direction of each of the first partition member 61, the second partition member 62, the third partition member 63, and the fourth partition member 64 are supported by the third wall portion 53 and the fourth wall portion 54.

One end of the first partition member 61 is connected to the first end portion 10, and the first partition member 61 extends from a connection portion thereof connected to the first end portion 10 toward the second end portion 20. The other end of the first partition member 61 is separated from the second end portion 20.

One end of the second partition member 62 is connected to the second end portion 20, and the second partition member 62 extends from a connection portion thereof connected to with the second end portion 20 toward the first end portion 10. The other end of the second partition member 62 is separated from the first end portion 10.

One end of the third partition member 63 is connected to the second end portion 20, and the third partition member 63 extends from a connection portion thereof connected to the second end portion 20 toward the first end portion 10. The other end of the third partition member 63 is separated from the first end portion 10.

One end of the fourth partition member 64 is connected to the first end portion 10, and the fourth partition member 64 extends from a connection portion thereof connected to the first end portion 10 toward the second end portion 20. The other end of the fourth partition member 64 is separated from the second end portion 20.

The intermediate portion 50 is positioned between the inflow portion 11 and the outflow portion 15. The intermediate portion 50 includes the branch flow path portions 80a, 80b and the merged flow path portion 90 defined by the wall portions 51 to 54 and the partition members 61 to 64. For example, the two branch flow path portions 80a, 80b sandwich the merged flow path portion 90 in the Z-axis direction. The plurality of branch flow path portions 80a, 80b are connected to the inflow portion 11 through the upstream flow path portion 12. The merged flow path portion 90 is connected to the downstream sides of the plurality of branch flow path portions 80a, 80b.

At least one of the branch flow path portions 80a, 80b includes a first flow path portion and a second flow path portion. In the present embodiment, the branch flow path portion 80a includes the first flow path portion 81a and the second flow path portion 82a, and the branch flow path portion 80b includes the first flow path portion 81b and the second flow path portion 82b.

The branch flow path portion 80a includes the first flow path portion 81a and the second flow path portion 82a. The first flow path portion 81a is formed upstream of the second flow path portion 82a, and the second flow path portion 82a is formed downstream of the first flow path portion 81a. The term upstream refers to a side relatively closer to the inflow portion 11 and the term downstream refers to a side relatively closer to the outflow portion 15 in the flow path from the inflow portion 11 toward the outflow portion 15.

The branch flow path portion 80b includes the first flow path portion 81b and the second flow path portion 82b. The first flow path portion 81b is formed upstream of the second flow path portion 82b, and the second flow path portion 82b is formed downstream of the first flow path portion 81b.

The first flow path portion 81a of the branch flow path portion 80a is defined by the first wall portion 51, the first partition member 61, the third wall portion 53, and the fourth wall portion 54. The second flow path portion 82a of the branch flow path portion 80a is defined by the first partition member 61, the second partition member 62, the third wall portion 53, and the fourth wall portion 54.

The first flow path portion 81b of the branch flow path portion 80b is defined by the second wall portion 52, the fourth partition member 64, the third wall portion 53, and the fourth wall portion 54. The second flow path portion 82b of the branch flow path portion 80b is defined by the third partition member 63, the fourth partition member 64, the third wall portion 53, and the fourth wall portion 54.

One end of each of the first flow path portions 81a, 81b is connected to the upstream flow path portion 12 formed in the interior of the first end portion 10. The first flow path portions 81a, 81b extend in a first direction d1 from respective connection portions connected to the upstream flow path portion 12. The first direction d1 is, for example, a direction parallel to the X-axis direction. The fluid flows through each of the first flow path portions 81a, 81b in the first direction d1. Further, the first direction d1 may be a direction inclined with respect to the X-axis direction.

The first flow path portion 81a of the branch flow path portion 80a is connected to the second flow path portion 82a through a space between the first partition member 61 and the second end portion 20, and the first flow path portion 81b of the branch flow path portion 80b communicates with the second flow path portion 82b through a space between the fourth partition member 64 and the second end portion 20.

The second flow path portions 82a, 82b respectively extend from portions communicating with the first flow path portions 81a, 81b in a direction different from the first direction d1, and the fluid flows in the second flow path portions 82a, 82b in a second direction d2. In the present embodiment, the second direction d2 is a direction opposite to the first direction d1.

The first flow path portions 81a, 81b, the second flow path portions 82a, 82b, and the merged flow path portion 90 are formed adjacent to one another in the Z-axis direction. The first flow path portion 81a of the branch flow path portion 80a is adjacent to the second flow path portion 82a of the branch flow path portion 80a with the first partition member 61 interposed therebetween. The first flow path portion 81b of the branch flow path portion 80b is adjacent to the second flow path portion 82b of the branch flow path portion 80b with the fourth partition member 64 interposed therebetween. The merged flow path portion 90 is adjacent to the second flow path portion 82a of the branch flow path portion 80a with the second partition member 62 interposed therebetween, and is adjacent to the second flow path portion 82b of the branch flow path portion 80b with the third partition member 63 interposed therebetween. In the Z-axis direction, the two second flow paths 82a, 82b are positioned between the two first flow path portions 81a, 81b, and the merged flow path portion 90 is positioned between the two second flow path portions 82a, 82b.

The second flow path portion 82a of the branch flow path portion 80a is connected to the merged flow path portion 90 through a space between the second partition member 62 and the first end portion 10. The second flow path portion 82b of the branch flow path portion 80b is connected to the merged flow path portion 90 through a space between the third partition member 63 and the first end portion 10. The merged flow path portion 90 extends in the X-axis direction from a portion connected to the two second flow path portions 82a, 82b and is connected to the outflow portion 15. The fluid flowing through the second flow path portions 82a, 82b merges into the merged flow path portion 90 and flows through the merged flow path portion 90 in the first direction d1.

A primary flow path portion 100 is formed between the inflow portion 11 and the outflow portion 15. The fluid flowing into the inflow portion 11 from outside the ultraviolet light fluid treatment device 1 flows through the primary flow path portion 100 and out of the outflow portion 15 to the outside of the ultraviolet light fluid treatment device 1. The primary flow path portion 100 includes the upstream flow path portion 12 formed in the first end portion 10, the branch flow path portions 80a, 80b formed in the intermediate portion 50, the merged flow path portion 90 formed in the intermediate portion 50, a first primary flow path portion 110 formed in the second end portion 20 (see FIG. 2), and a second primary flow path portion 120 formed in the second end portion 20 (see FIG. 3). Further, one or more structural elements that configure the primary flow path portion 100 (e.g., a part of the first end portion 10, the intermediate portion 50, and the second end portion 20) may be referred to as a primary conduit.

The first primary flow path portion 110 is formed upstream of the second primary flow path portion 120, and is connected to the merged flow path portion 90 of the primary flow path portion 100. As illustrated in FIG. 2, the two second light sources 72 sandwich the first primary flow path portion 110 in the Z-axis direction. The second primary flow path portion 120 is formed downstream of the first primary flow path portion 110, and is connected to the outflow portion 15. The first primary flow path portion 110 and the second primary flow path portion 120 are connected to each other in the direction of flow of the fluid (X-axis direction in FIG. 2) and pass through the inner member 21.

A cross sectional area of the second primary flow path portion 120 orthogonal to the direction of flow of the fluid (X-axis direction in FIG. 2) is smaller than an area of the cross section of the first primary flow path portion 110 orthogonal to the X-axis direction. Further, the cross-sectional area of the second primary flow path portion 120 orthogonal to the X-axis direction is smaller than a cross sectional area of the outflow portion 15 orthogonal to the X-axis direction.

The second end portion 20 includes a secondary flow path portion 200 connected to the primary flow path portion 100. The secondary flow path portion 200 is connected to a portion of the primary flow path portion 100 via a first connection portion 230 and a second connection portion 240. For example, the first connection portion 230 is formed in the first primary flow path portion 110, and connects the first primary flow path portion 110 and the secondary flow path portion 200. The second connection portion 240 is formed in the second primary flow path portion 120, and connects the second primary flow path portion 120 and the secondary flow path portion 200. One or more structural elements that configure the secondary flow path portion 200 (e.g., a part of the second end portion 20) may be referred to as a secondary conduit.

A cross sectional area of the secondary flow path portion 200 orthogonal to the direction of flow of the fluid (i.e., direction from the first connection portion 230 toward the second connection portion 240) is smaller than a cross sectional area of each of the flow path portions 12, 80a, 80b, 90, 110, 120 included in the primary flow path portion 100, the cross section being orthogonal to the direction of flow of the fluid.

The second connection portion 240 is formed downstream of the first connection portion 230 in the X-axis direction. The first connection portion 230 and the second connection portion 240 are formed closer to the outflow portion 15 than are the second light sources 72 in the X-axis direction.

The inner member 21 includes a first surface 21b (illustrated in FIG. 3) facing the outer member 22 and a second surface 21d (illustrated in FIG. 1) positioned on a side opposite to the first surface 21b. A secondary partition member 251 is disposed on the first surface 21b of the inner member 21. For example, two of the secondary partition members 251 sandwich the second primary flow path portion 120 in the Y-axis direction. Each of the secondary partition members 251 extends in the Z-axis direction. A wall portion 21c surrounding the first surface 21b is disposed on an outer edge of the first surface 21b.

The outer member 22 includes a first surface 22b (illustrated in FIG. 3) facing the inner member 21 and a second surface 22d (illustrated in FIG. 2) positioned on a side opposite to the first surface 22b. The inner member 21 is coupled to the outer member 22 with the first surface 21b, on which the secondary partition members 251 and the wall portion 21c are disposed, facing the first surface 22b of the outer member 22. The second connection portion 240 opens to the first surface 22b of the outer member 22. The second connection portion 240 is connected to the outflow portion 15 in the X-axis direction. A width of the second connection portion 240 in the Z-axis direction is smaller than a diameter of the outflow portion 15. A width of the second connection portion 240 in the Y-axis direction is larger than the diameter of the outflow portion 15.

The secondary flow path portion 200 is defined by the first surface 21b of the inner member 21, the secondary partition members 251, the wall portion 21c, and the first surface 22b of the outer member 22. The secondary flow path portion 200 includes a first secondary flow path portion 210 and a second secondary flow path portion 220. In the direction of flow of the fluid through the secondary flow path portion 200, the first secondary flow path portion 210 is connected to the first connection portion 230 side upstream of the second secondary flow path portion 220, and the second secondary flow path portion 220 is connected to the second connection portion 240 side downstream of the first secondary flow path portion 210.

The fluid flowing from the merged flow path portion 90 to the outflow portion 15 is divided into a primary flow and a secondary flow. The primary flow flows from the merged flow path portion 90 through the first primary flow path portion 110 and the second primary flow path portion 120 without passing through the secondary flow path portion 200. The secondary flow flows from the merged flow path portion 90 through the first connection portion 230 and into the secondary flow path portion 200. The secondary flow flowing into the secondary flow path portion 200 flows through the first secondary flow path portion 210 and the second secondary flow path portion 220 in this order, and then through the second connection portion 240 and merges with the primary flow and flows out to the outflow portion 15.

The first secondary flow path portion 210 extends in a direction away from the first primary flow path portion 110 and the second primary flow path portion 120 of the primary flow path portion 100 in the Z-axis direction orthogonal to a direction of flow of the primary flow of the primary flow path portion 100 (X-axis direction in FIGS. 2 and 3). Two of the first secondary flow path portions 210 sandwich the second primary flow path portion 120 in the Z-axis direction, and the first secondary flow path portions 210 extend from the second primary flow path portion 120 in directions opposite each other. Each of the first secondary flow path portions 210 extends in a direction away from the second primary flow path portion 120 of the primary flow path portion 100, in the Z-axis direction.

The two second secondary flow path portions 220 sandwich the first secondary flow path portions 210 in the Y-axis direction. The secondary partition members 251 are positioned between the first secondary flow path portions 210 and the second secondary flow path portions 220 in the Y-axis direction. The first secondary flow path portions 210 and the second secondary flow path portions 220 are adjacent to the secondary partition members 251 in the Y-axis direction.

The second secondary flow path portions 220 extend in directions different from extending directions of the first secondary flow path portions 210. For example, the second secondary flow path portions 220 extend in directions approaching the second primary flow path portion 120 and the second connection portion 240, in the Z-axis direction.

As illustrated in FIG. 2, the first light source 71 is disposed at a position at which the merged flow path portion 90 can be irradiated with ultraviolet light. For example, the first light source 71 is disposed in the first light source placement portion 13 formed in the first end portion 10, and the first surface (i.e., light-emitting surface) 71a of the first light source 71 faces a merging portion of the two second flow path portions 82a, 82b into the merged flow path portion 90 with the first window portion 14 interposed therebetween. The ultraviolet light emitted from the first surface 71a of the first light source 71 is irradiated from the merging portion side of the second flow path portions 82a, 82b into the merged flow path portion 90.

One or more second light sources 72 are disposed at a position at which one branch flow path portion can be irradiated with ultraviolet light. In the example illustrated in FIG. 2, the second light sources 72 are disposed at positions at which the respective branch flow path portions 80a, 80b can be irradiated with ultraviolet light. For example, the second light source 72 is disposed in the second light source placement portion 16 formed in the second end portion 20. At least one of the two second light sources 72 is disposed at a position at which at least one of the first flow path portions 81a, 81b and the second flow path portions 82a, 82b can be irradiated with ultraviolet light. In the present embodiment, one of the second light sources 72 is disposed at a position facing a region where the first flow path portion 81a and the second flow path portion 82a of the branch flow path portion 80a are connected, with the second window portion 17 interposed therebetween. The other of the second light sources 72 is disposed at a position facing a region where the first flow path portion 81b and the second flow path portion 82b of the branch flow path portion 80b are connected with the second window portion 17 interposed therebetween.

The ultraviolet light output from the first surface 72a of one of the second light sources 72 is irradiated from the connection portion side of the first flow path portion 81a and the second flow path portion 82a into the first flow path portion 81a and the second flow path portion 82a. The ultraviolet light output from the first surface 72a of the other of the second light sources 72 is irradiated from the connection portion side of the first flow path portion 81b and the second flow path portion 82b into the first flow path portion 81b and the second flow path portion 82b. The second surface 72b of the second light source 72 is positioned between the first surface 72a and the secondary flow path portion 200 in the X-axis direction.

Next, a fluid treatment that uses the ultraviolet light fluid treatment device 1 according to the present embodiment will be described.

The ultraviolet light fluid treatment device 1 treats a fluid such as a liquid or a gas by irradiating the fluid with ultraviolet light. For example, water can be irradiated with ultraviolet light to reduce the number of bacteria and viruses in the water after treatment compared to before the treatment.

The inflow portion 11 is connected to piping on the upstream side of the ultraviolet light fluid treatment device 1 directly or via a joint member. The outflow portion 15 is connected to piping downstream of the ultraviolet light fluid treatment device 1 directly or via a joint member. The fluid flowing through upstream the external piping flows into the inflow portion 11 and branches into two in the upstream flow path portion 12. One portion of the fluid branched into two flows into the first flow path portion 81a of the branch flow path portion 80a, and the other portion of the branched fluid flows into the first flow path portion 81b of the branch flow path portion 80b.

The fluid flowing into the first flow path portions 81a, 81b respectively flows through the first flow path portions 81a, 81b in the first direction d1, and into the second flow path portions 82a, 82b at the ends of the first flow path portions 81a, 81b on the second end portion 20 side. The fluid flowing into the second flow path portions 82a, 82b respectively flows through the second flow path portions 82a, 82b in the second direction d2. The fluid flowing through the first flow path portions 81a, 81b and the second flow path portions 82a, 82b is irradiated with ultraviolet light from the second light sources 72.

The fluid flowing into the second flow path portions 82a, 82b in the second direction d2 merges and flows into the merged flow path portion 90. The fluid flowing into the merged flow path portion 90 flows through the merged flow path portion 90 in the first direction d1. The fluid flowing through the merged flow path portion 90 is irradiated with ultraviolet light from the first light source 71. The fluid flowing through the merged flow path portion 90 flows through the outflow portion 15 and out to external downstream piping connected to the outflow portion 15.

According to the present embodiment, the fluid flowing into the interior of the ultraviolet light fluid treatment device 1 from the inflow portion 11 is branched a plurality of times, merges once again, and flows out of the outflow portion 15. As a result, a flow path length of the fluid flowing between external upstream piping connected to the inflow portion 11 and external downstream piping connected to the outflow portion 15 can be made longer compared to a case in which the fluid flows from the inflow portion 11 to the outflow portion 15 without being branched. Then, the fluid flowing through each of the branch flow path portions 80a, 80b is irradiated with ultraviolet light from the second light source 72 and further merges in the merged flow path portion 90 from the branch flow path portions 80a, 80b, and the fluid flowing through the merged flow path portion 90 is irradiated with ultraviolet light from the first light source 71. As a result, an integrated luminance of the fluid flowing through the interior of the ultraviolet light fluid treatment device 1 by the ultraviolet light can be increased, and a treatment effect of the ultraviolet light on the fluid can be enhanced.

The fluid flowing through the merged flow path portion 90 flows into the first primary flow path portion 110. A portion of the fluid flowing through the first primary flow path portion 110 flows from the first connection portion 230 to the first secondary flow path portion 210, and flows through the first secondary flow path portion 210 in a direction away from the first connection portion 230 in the Z-axis direction. The fluid flowing through the space between both ends in the Z-axis direction of the secondary partition member 251 and the wall portion 21c and through the first secondary flow path portion 210 flows into the second secondary flow path portion 220, and thus the flow is reversed in the Z-axis direction. The fluid reversed in flow flows from the connection portion with the first secondary flow path portion 210 and through the second secondary flow path portion 220 in a direction approaching the second connection portion 240 in the Z-axis direction, and flows out of the second connection portion 240 toward the outflow portion 15.

The second light source 72 can be cooled from the second surface 72b side by the fluid flowing through this secondary flow path portion 200. This makes it possible to suppress a decrease in light emission efficiency due to the heat generation associated with the light emission of the second light source 72.

The cross-sectional area of the secondary flow path portion 200 orthogonal to the direction of flow of the fluid is smaller than the cross-sectional area of the first primary flow path portion 110 and the cross-sectional area of the second primary flow path portion 120 between the merged flow path portion 90 and the outflow portion 15, the cross sections being orthogonal to the direction of flow of the primary flow.

Accordingly, a flow rate of the primary flow flowing between the merged flow path portion 90 and the outflow portion 15 is greater than a flow rate of the secondary flow flowing through the secondary flow path portion 200. Furthermore, the second light source 72 is not positioned in the flow path portion between the merged flow path portion 90 and the outflow portion 15, and does not hinder the flow of the fluid in the primary flow path portion 100. As a result, according to the present embodiment, the second light source 72 can be cooled by the fluid without the flow of the fluid from the merged flow path portion 90 toward the outflow portion 15 being hindered, that is, while a pressure loss of the fluid in the ultraviolet light fluid treatment device 1 is suppressed.

Further, with the fluid flowing from the two secondary flow path portions (i.e., first secondary flow path portion 210 and second secondary flow path portion 220) in different directions, a flow path length of the fluid flowing through the secondary flow path portion 200 can be increased while suppressing an increase in size of the ultraviolet light fluid treatment device 1, making it possible to enhance a cooling efficiency of the second light sources 72. For example, the first secondary flow path portion 210 and the second secondary flow path portion 220 flow in directions opposite each other in the Z-axis direction, making it possible to suppress an increase in the size of the member in which the secondary flow path portion 200 is disposed in the Y-axis direction.

Figure 4:
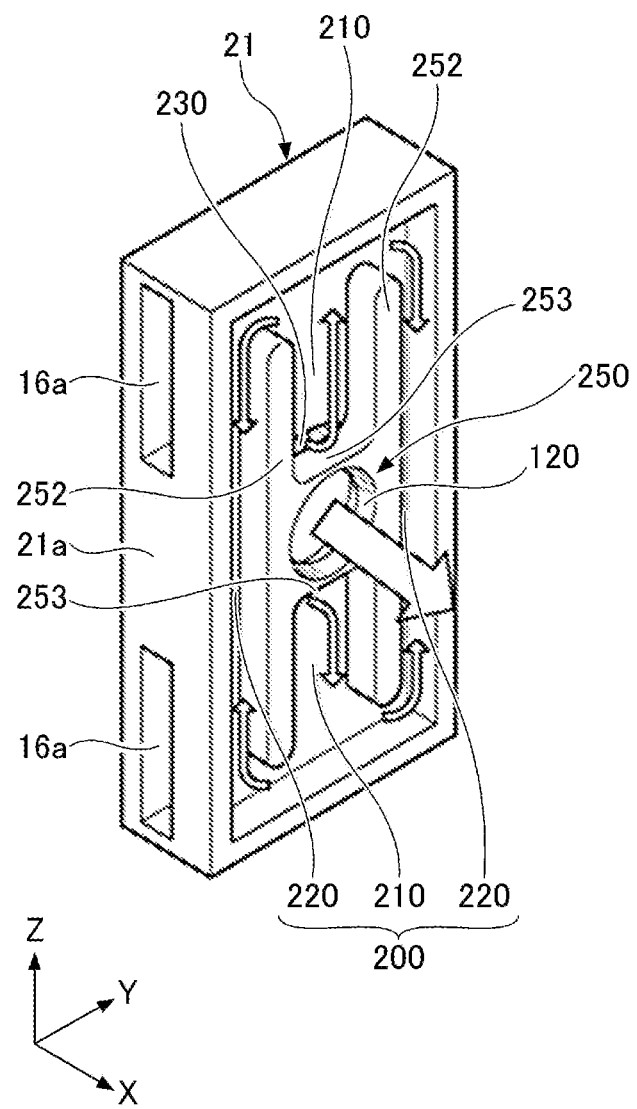
FIG. 4 illustrates a schematic perspective view of another example of an inner member of the second end portion in the ultraviolet light fluid treatment device FIG. 5A schematically illustrates a plan view of a first modified example of the ultraviolet light fluid treatment device.

FIG. 4 illustrates a perspective view of an example of a secondary partition member 250, which can be replaced with the secondary partition member 251 described above.

The secondary partition member 250 includes two first partition portions 252 extending in the Z-axis direction and two second partition portions 253 extending in the Y-axis direction.

The two first partition portions 252 are positioned between the first secondary flow path portions 210 and the second secondary flow path portions 220 in the Y-axis direction. The first secondary flow path portions 210 and the second secondary flow path portions 220 are adjacent to the first partition portions 252 in the Y-axis direction.

The two second partition portions 253 are positioned away from each other in the Z-axis direction. The second primary flow path portion 120 is positioned between the two second partition portions 253 in the Z-axis direction. Each second partition portion 253 is connected to the two first partition portions 252 in the Y-axis direction. Each second partition portion 253 partitions the first connection portion 230 and the second primary flow path portion 120 in the Z-axis direction. The first connection portion 230 is positioned between the second partition portions 253 and the first secondary flow path portions 210 in the Z-axis direction. With the first connection portion 230 and the second primary flow path portion 120 being partitioned by the second partition portions 253, the secondary flow can readily flow from the first primary flow path portion 110, through the first connection portion 230, and to the first secondary flow path portions 210.

Figure 5A:
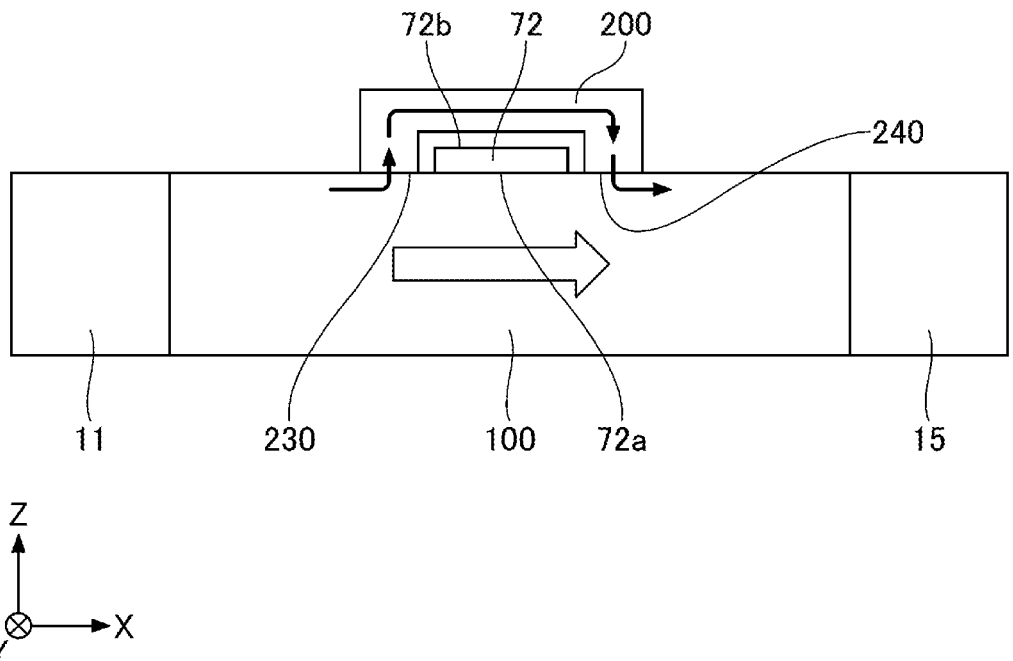
FIG. 5B schematically illustrates a plan view of a second modified example of the ultraviolet light fluid treatment device.
FIG. 5C schematically illustrates a plan view of a third modified example of the ultraviolet light fluid treatment device.

In another implementation, as schematically illustrated in FIG. 5A, the second light source 72 may be configured to irradiate the primary flow path portion 100 with ultraviolet light from the Z-axis direction orthogonal to the direction of flow of the fluid (X-axis direction). In the Z-axis direction, the second light source 72 is positioned between the primary flow path portion 100 and the secondary flow path portion 200. The first surface (i.e., light output surface) 72a of the second light source 72 faces the primary flow path portion 100, and the second surface 72b faces the secondary flow path portion.

The first connection portion 230 is formed upstream of the second connection portion 240 in the X-axis direction. The first connection portion 230 is formed upstream of the second light source 72 in the X-axis direction. The second connection portion 240 is formed downstream of the second light source 72 in the X-axis direction.

Figure 5B:
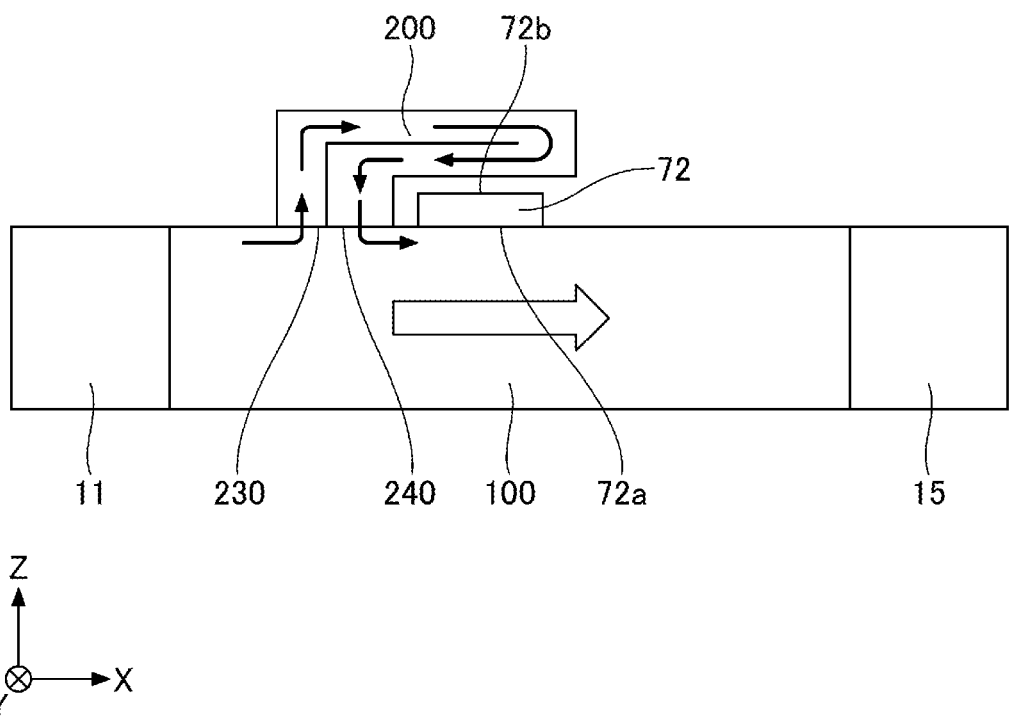

In another implementation, as illustrated in FIG. 5B, the first connection portion 230 and the second connection portion 240 may be formed upstream of the second light source 72 in the X-axis direction. The first connection portion 230 is formed upstream of the second connection portion 240 in the X-axis direction.

Figure 5C:
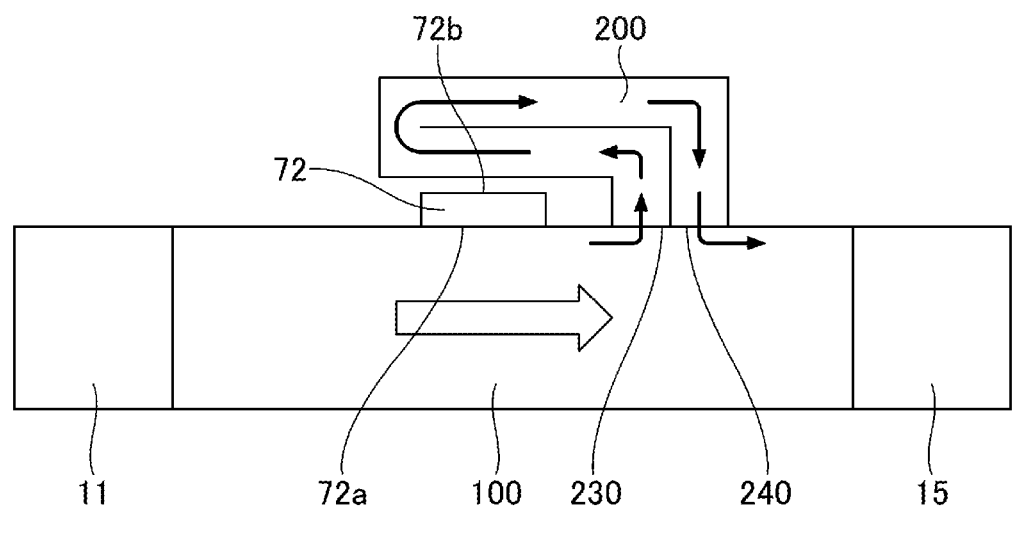

In another implementation, as illustrated in FIG. 5C, the first connection portion 230 and the second connection portion 240 may be formed downstream of the second light source 72 in the X-axis direction. The first connection portion 230 is formed upstream of the second connection portion 240 in the X-axis direction.

Further, the first connection portion 230 may be formed downstream of the second connection portion 240 in the X-axis direction, and the second connection portion 240 may be formed upstream of the first connection portion 230 in the X-axis direction. In this case, a mechanism such as a check valve, for example, for inhibiting backflow of the fluid from the second connection portion 240 to the first connection portion 230 is preferably formed in at least any one of the first connection portion 230, the second connection portion 240, and the secondary flow path portion 200.

Figure 6A:
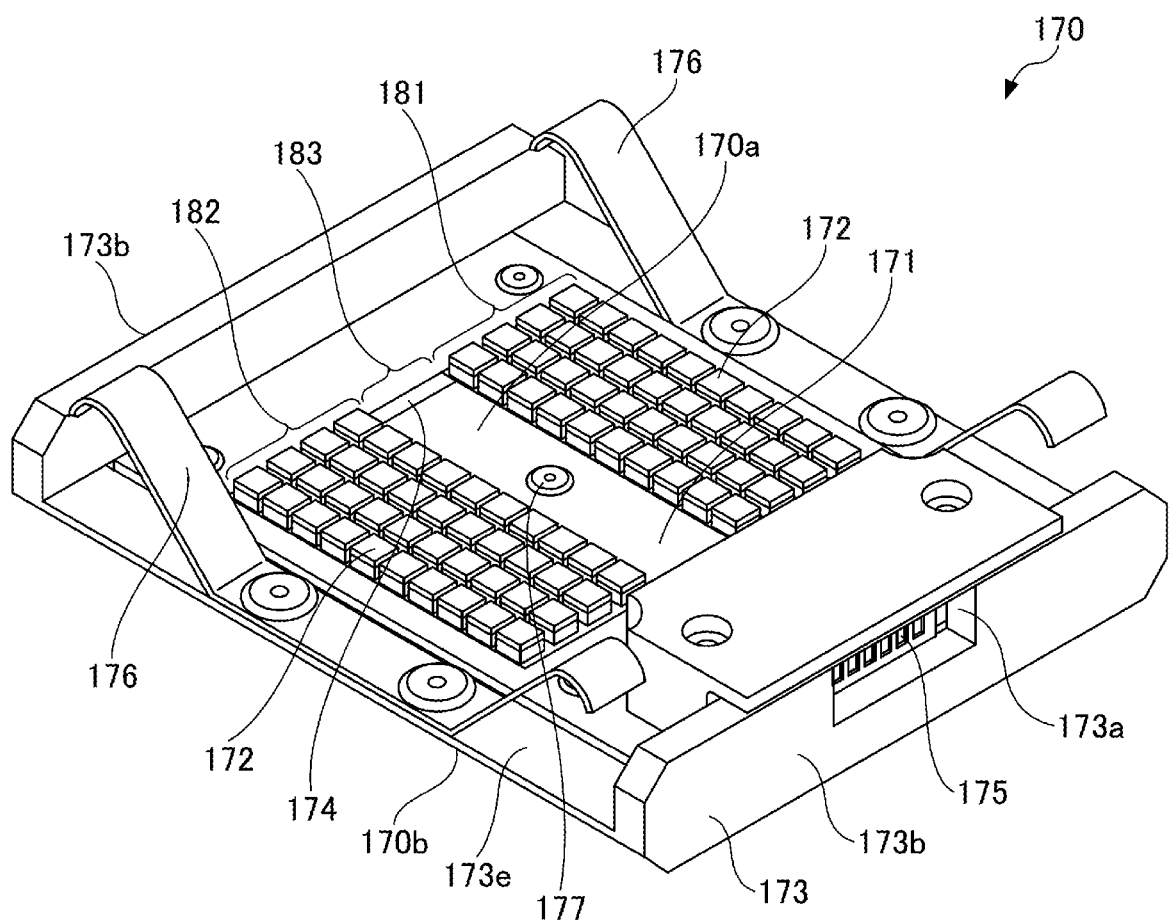
FIG. 6A schematically illustrates a perspective view of an example of a light source in the embodiment.

A light source 170 illustrated in FIG. 6A can be used as the first light source or the second light source described above.

The light source 170 includes a wiring substrate 171 and a plurality of light-emitting elements. The light-emitting elements are mounted on a surface of the wiring substrate 171. In a plan view as viewed from the surface side of the wiring substrate 171, the wiring substrate 171 has, for example, a quadrangular shape, and a center of the wiring substrate 171 is positioned at an intersection of two diagonal lines in this quadrangular shape. The wiring substrate 171 includes a first region 181 and a second region 182. The first region 181 and the second region 182 are aligned in one direction of the wiring substrate 171. The wiring substrate 171 can further include a third region 183. The third region 183 is positioned between the first region 181 and the second region 182 in a plane parallel to the surface of the wiring substrate 171. The third region 183 includes the center of the wiring substrate 171. In a case in which the third region 183 is not disposed, the center of the wiring substrate 171 is positioned at a boundary between the first region 181 and the second region 182, for example. The first region 181 or the second region 182 may include the center of the wiring substrate 171. A width of the third region 183 in the direction in which the first region 181, the third region 183, and the second region 182 are aligned is preferably the same as or wider than a thickness of the first partition member 61 and the fourth partition member 64.

In the example illustrated in FIG. 6A, a plurality of housings 172 are mounted in the first region 181. A plurality of the housings 172 are mounted in the second region 182. One housing 172 includes at least one light-emitting element. The housing 172 can also include a lens disposed on the light-emitting element. Alternatively, light-emitting elements not housed in the housings 172 may be disposed in the first region 181 and the second region 182. No light-emitting element is disposed in the third region 183.

The light source 170 can include a holding member 173 that holds the wiring substrate 171. The holding member 173 includes a surface 173e on which the wiring substrate 171 is mounted, and a surface positioned on a side opposite to the surface 173e. The wiring substrate 171 is fixed to the surface 173e of the wiring substrate 171 by, for example, a screw or an adhesive. The surface of the wiring substrate 171 on which the housings 172 including the light-emitting elements are mounted is a first surface 170a of the light source 170, and the surface of the holding member 173 positioned on the side opposite to the surface 173e is a second surface 170b of the light source 170. The holding member 173 includes a wall portion 173b covering an end portion of the wiring substrate 171 on the first surface 170a side of the light source 170. For example, a pair of the wall portions 173b sandwich the wiring substrate 171 in a plan view of the first surface 170a.

In the light source 170, a wire 174 electrically connected to the light-emitting elements can be disposed on the surface of the wiring substrate 171. Further, a connector 175 electrically connected to the wire 174 can be disposed on the surface of the wiring substrate 171. An insertion port 173a exposing the connector 175 from the holding member 173 is disposed in one of the wall portions 173b of the holding member 173.

A spring member 176 is disposed on the first surface 170a side of the light source 170. The spring member 176 is, for example, a metal leaf spring, and an example of an elastic member. For example, a pair of the spring members 176 sandwich the wiring substrate 171 in a plan view of the first surface 170a, and are fixed to the holding member 173.

The light source 170 can be disposed as the first light source in the first light source placement portion 13 illustrated in FIG. 2. The first surface 170a of the light source 170 disposed in the first light source placement portion 13 faces the first window portion 14. The ultraviolet light output from the first surface 170a is irradiated onto the fluid flowing through the merged flow path portion 90 via the first window portion 14.

The light source 170 is disposed in the first light source placement portion 13 with the spring members 176 being elastically deformed from a natural state. The spring members 176 disposed on the first surface 170a side is in contact with the first window portion 14. By a restoring force of the spring members 176, the light source 170 is urged toward a first partition wall 13b partitioning the upstream flow path portion 12 and the first light source placement portion 13, and the second surface 170b is pressed against the first partition wall 13b. This makes it possible to increase the cooling efficiency of the light source 170 by the fluid flowing through the upstream flow path portion 12.

Further, the light source 170 can be disposed as the second light source in the second light source placement portion 16 illustrated in FIG. 2. The first surface 170a of the light source 170 disposed in the second light source placement portion 16 faces the second window portion 17. The ultraviolet light output from the first surface 170a is irradiated into the fluid flowing through the branch flow path portions 80a, 80b via the second window portion 17.

The light source 170 is disposed in the second light source placement portion 16 with the spring members 176 being elastically deformed from the natural state. The spring members 176 provided on the first surface 170a side is in contact with the second window portion 17. By the restoring force of the spring members 176, the light source 170 is urged toward a second partition wall 16b partitioning the secondary flow path portion 200 and the second light source placement portion 16, and the second surface 170b is pressed against the second partition wall 16b. This makes it possible to increase the cooling efficiency of the light source 170 by the fluid flowing through the secondary flow path portion 200.

The first region 181 of the light source 170 disposed in the second light source placement portion 16 facing the branch flow path portion 80a of the pair of branch flow path portions 80a, 80b faces the first flow path portion 81a, and the light-emitting elements disposed in the first region 181 irradiate the fluid flowing through the first flow path portion 81a with ultraviolet light. The second region 182 of the light source 170 disposed in the second light source placement portion 16 facing the branch flow path portion 80a faces the second flow path portion 82a, and the light-emitting elements disposed in the second region 182 irradiate the fluid flowing through the second flow path portion 82a with ultraviolet light.

The first region 181 of the light source 170 disposed in the second light source placement portion 16 facing the branch flow path portion 80b faces the second flow path portion 82b, and the light-emitting elements disposed in the first region 181 irradiate the fluid flowing through the second flow path portion 82b with ultraviolet light. The second region 182 of the light source 170 disposed in the second light source placement portion 16 facing the branch flow path portion 80b faces the first flow path portion 81b, and the light-emitting elements disposed in the second region 182 irradiate the fluid flowing through the first flow path portion 81b with ultraviolet light. The ultraviolet light from the light-emitting elements can be irradiated in each of the extending directions of the first flow path portions 81a, 81b and the second flow path portions 82a, 82b, making it possible to increase the integrated luminance. As the light-emitting elements disposed in the first region 181 and the light-emitting elements disposed in the second region 182, the same light-emitting elements can be used. As the light-emitting elements disposed in the first region 181 and the light-emitting elements disposed in the second region 182, light-emitting elements having different emission peak wavelengths may be used.

The third region 183 of the light source 170 disposed in the second light source placement portion 16 facing the branch flow path portion 80a faces the first partition member 61 with a region where the first flow path portion 81a and the second flow path portion 82a of the branch flow path portion 80a communicate interposed therebetween. Light-emitting elements are not disposed in the third region 183 facing the first partition member 61. The third region 183 of the light source 170 disposed in the second light source placement portion 16 facing the branch flow path portion 80b faces the fourth partition member 64 with a region where the first flow path portion 81b and the second flow path portion 82b of the branch flow path portion 80b communicate interposed therebetween. No light-emitting element is not disposed in the third region 183 facing the fourth partition member 64. Due to the ultraviolet light from the light-emitting elements disposed in the first region 181 and the second region 182, the integrated luminance of the fluid flowing through each branch flow path portion 80a, 80b by the ultraviolet light can be sufficiently obtained, making it possible to reduce the number of light-emitting elements while ensuring the treatment effect of the ultraviolet light on the fluid by using a structure in which no light-emitting element is disposed in the third region 183.

In the third region 183 in which no light-emitting element is disposed, a screw 177 illustrated in FIG. 6A can be disposed. With this screw 177, the third region 183, which is a region including the center of the wiring substrate 171, can be fixed to the holding member 173. In addition, for example, four corners of the wiring substrate 171 are fixed to the holding member 173 by screws. With the third region 183 including the center of the wiring substrate 171 fixed to the holding member 173 by the screw 177, a center portion of the wiring substrate 171 can be suppressed from significantly being loosen from the holding member 173, making it possible to adhere the wiring substrate 171 to the holding member 173. This makes it possible to reduce a gap between the wiring substrate 171 and the first partition wall 13b and increase the cooling efficiency of the light source 170 by the fluid flowing through the upstream flow path portion 12. Further, a gap between the wiring substrate 171 and the second partition wall 16b can be reduced, making it possible to increase the cooling efficiency of the light source 170 by the fluid flowing through the secondary flow path portion 200.

Figure 6B:
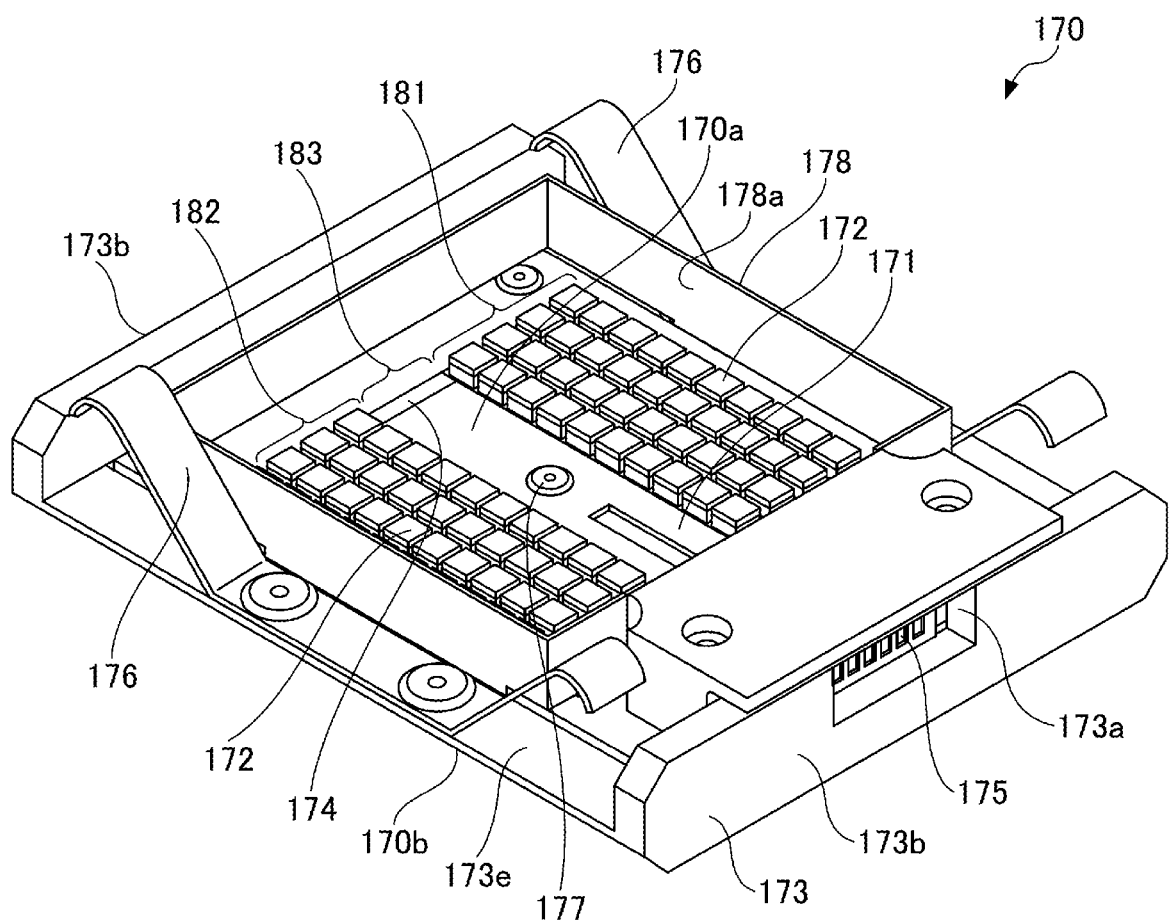
FIG. 6B schematically illustrates a perspective view of another example of the light source.

Further, the light source 170 may include a light-reflecting member. FIG. 6B is a schematic perspective view illustrating another example of the light source of an embodiment of the present disclosure, and illustrates the light source 170 including a light-reflecting member 178.

The light-reflecting member 178 has, for example, a shape such as a polygon or a circle in a plan view as viewed from the surface side of the wiring substrate 171. In the example illustrated in FIG. 6B, the light-reflecting member 178 has a substantially rectangular frame shape in a plan view as viewed from the surface side of the wiring substrate 171. Further, the light-reflecting member 178 is a member having a predetermined height from the surface of the wiring substrate 171. The light-reflecting member 178 surrounds the first region 181, the second region 182, and the third region 183 in a plan view as viewed from the surface side of the wiring substrate 171.

The light-reflecting member 178 contains, for example, a metal material or a resin material. As the metal material, a material of which surface is treated with aluminum, stainless steel, or the like can be used. As the resin material, a fluororesin or the like can be used.

The light-reflecting member 178 reflects light from the light-emitting elements included in the first region 181 and the second region 182 to an inner side the light-reflecting member 178 by an inner surface 178a to suppress, of the light from the light-emitting elements, light output to an outer side of the light-reflecting member 178. As a result, a light extraction efficiency of the light source 170 can be increased.

The inner surface 178a of the light-reflecting member 178 is preferably a surface having high reflectivity with respect to the ultraviolet light emitted from the light-emitting elements in order to suppress light loss due to light absorption, light scattering, or the like. Such a surface can be, for example, a surface having a reflectivity of 60% or greater and preferably 90% or greater with respect to the ultraviolet light emitted from the light-emitting elements. It is noted that a member having light absorbency may be employed instead of the light-reflecting member 178.

As the first light source and the second light source described above, a light source 270 illustrated in FIGS. 7 and 8 can be used. The light source 270 has a waterproof structure that shields the light-emitting elements and the wiring substrate from water by the light source itself. In the following, the configuration common to that of the light source 170 will be omitted as appropriate.

Figure 7:
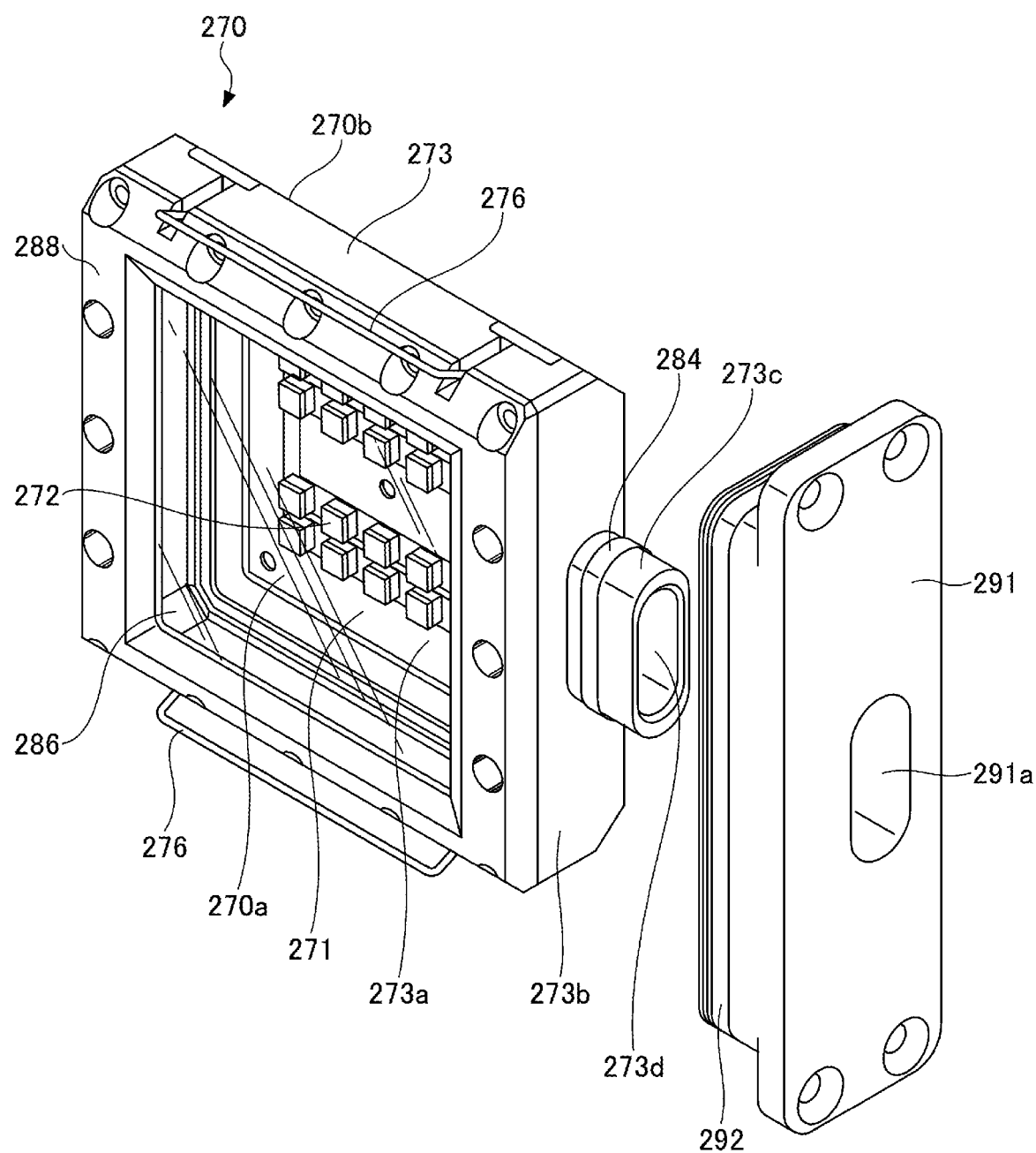
FIG. 7 schematically illustrates a perspective view of said another example of the light source.
Figure 8:
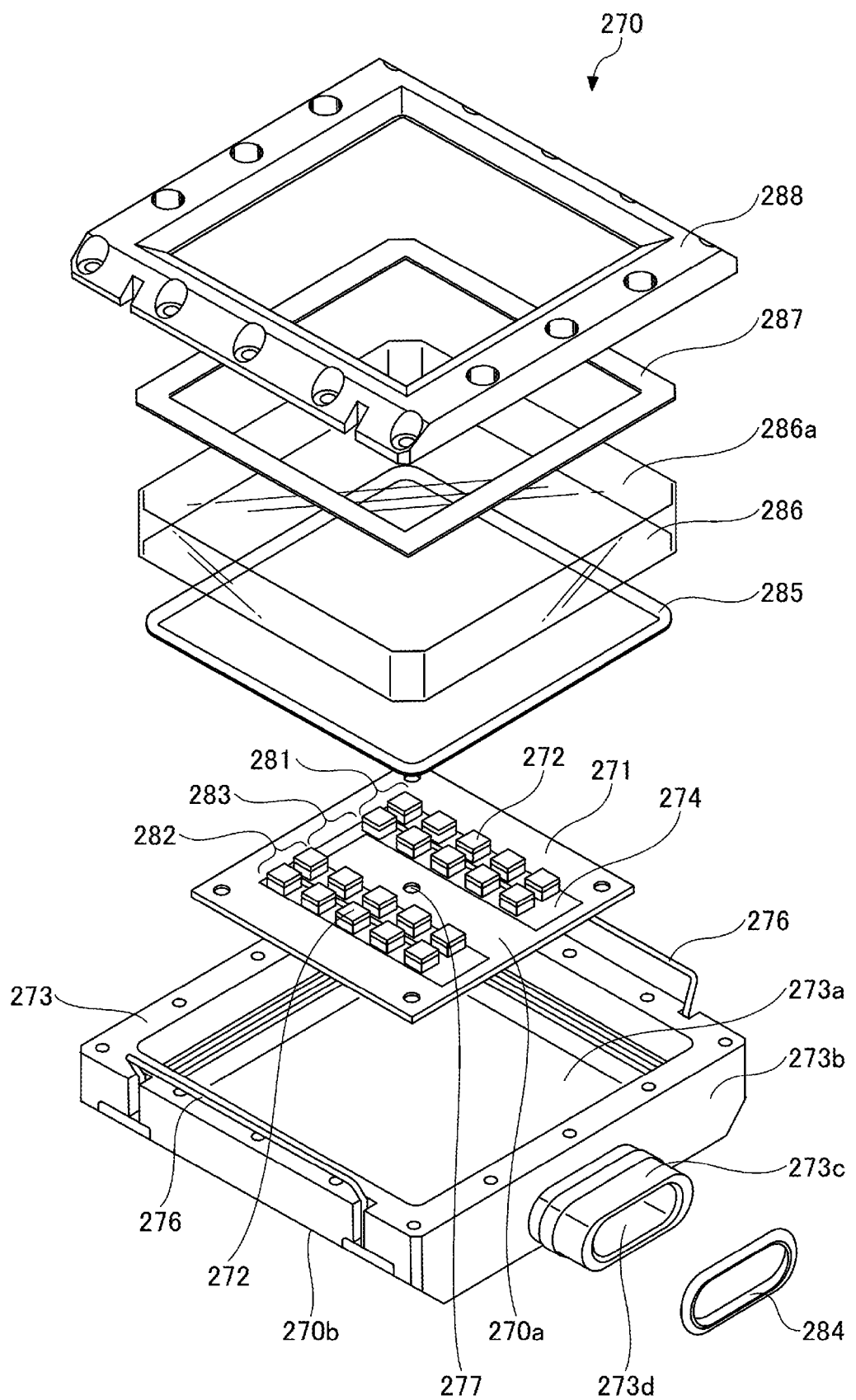
FIG. 8 illustrates an exploded perspective view of the light source illustrated in FIG. 7.

In the light source 270 illustrated in FIGS. 7 and 8, a surface of a holding member 273 and wall portions 273b define a recessed portion 273a. A wiring substrate 271 is disposed in the recessed portion 273a of the holding member 273.

An opening of the recessed portion 273a of the holding member 273 is closed by a cover glass 286 made of synthetic quartz, for example. A ring 285 for waterproofing is interposed between the cover glass 286 and the holding member 273. The light source 270 may include a frame member 288 disposed on the wall portions 273b of the holding member 273. The frame member 288 can be an annular quadrangular outer shape in a plan view as viewed from a first surface 270a side of the light source 270. The cover glass 286 is interposed between the frame member 288 and the holding member 273. The frame member 288 is fixed to the holding member 273 by a screw, for example, while a peripheral portion of a surface 286a of the cover glass 286 (surface positioned on a side opposite to a surface facing the wiring substrate 271) is pressed toward the holding member 273. A cushioning material 287 is interposed between the peripheral portion of the surface 286a of the cover glass 286 and the frame member 288. Note that the frame member 288 may be fixed by an adhesive. Further, in the light source 270, the light-reflecting member 178 such as illustrated in FIG. 6B may be disposed in the recessed portion 273a.

A cylindrical portion 273c in which a first through hole 273d leading into the recessed portion 273a is formed is provided on one side surface lateral surface of the wall portions 273b defining the recessed portion 273a of the holding member 273.

The light source 270 can be disposed as the first light source in the first light source placement portion 13 through the first opening 13a illustrated in FIG. 2. Further, the light source 270 can be disposed as the second light source in the second light source placement portion 16 through the second opening 16a illustrated in FIG. 2. With the light source 270 disposed in the first light source placement portion 13, the first opening 13a is covered with a waterproof cap 291 illustrated in FIG. 7. A waterproof ring 292 is interposed between the waterproof cap 291 and an inner wall of the first opening 13a.

The waterproof cap 291 has a second through hole 291a. An opening shape of the second through hole 291a is preferably substantially the same as that of the cylindrical portion 273c as viewed from an opening direction of the first through hole 273d of the light source 270. The light source 270 is disposed in the first light source placement portion 13 and, with the waterproof cap 291 mounted on the first opening 13a, the cylindrical portion 273c provided in the holding member 273 fits into the second through hole 291a. A waterproof ring 284 is interposed between the cylindrical portion 273c and an inner wall of the second through hole 291a. As a result, a gap between the second through hole 291a and the cylindrical portion 273c can be reduced, and water can be prevented from coming into the first light source placement portion 13. In the light source 270, an electrical cable electrically connected to a wire 274 of the wiring substrate 271 can be disposed on the surface of the wiring substrate 271. In this case, the electrical cable can be pulled out of the light source 270 through the first through hole 273d of the holding member 273 and the second through hole 291a of the waterproof cap 291.

Fluid Retention in Embodiments

In an embodiment, a portion of the fluid flowing through the interior of the ultraviolet light fluid treatment device 1 is retained, thereby increasing the integrated luminance of the ultraviolet light onto the fluid in accordance with a retention time, and thus making it possible to increase the treatment effect of the ultraviolet light on the fluid. This fluid retention will be described in detail below.

First Example of Fluid Retention

Figure 9:
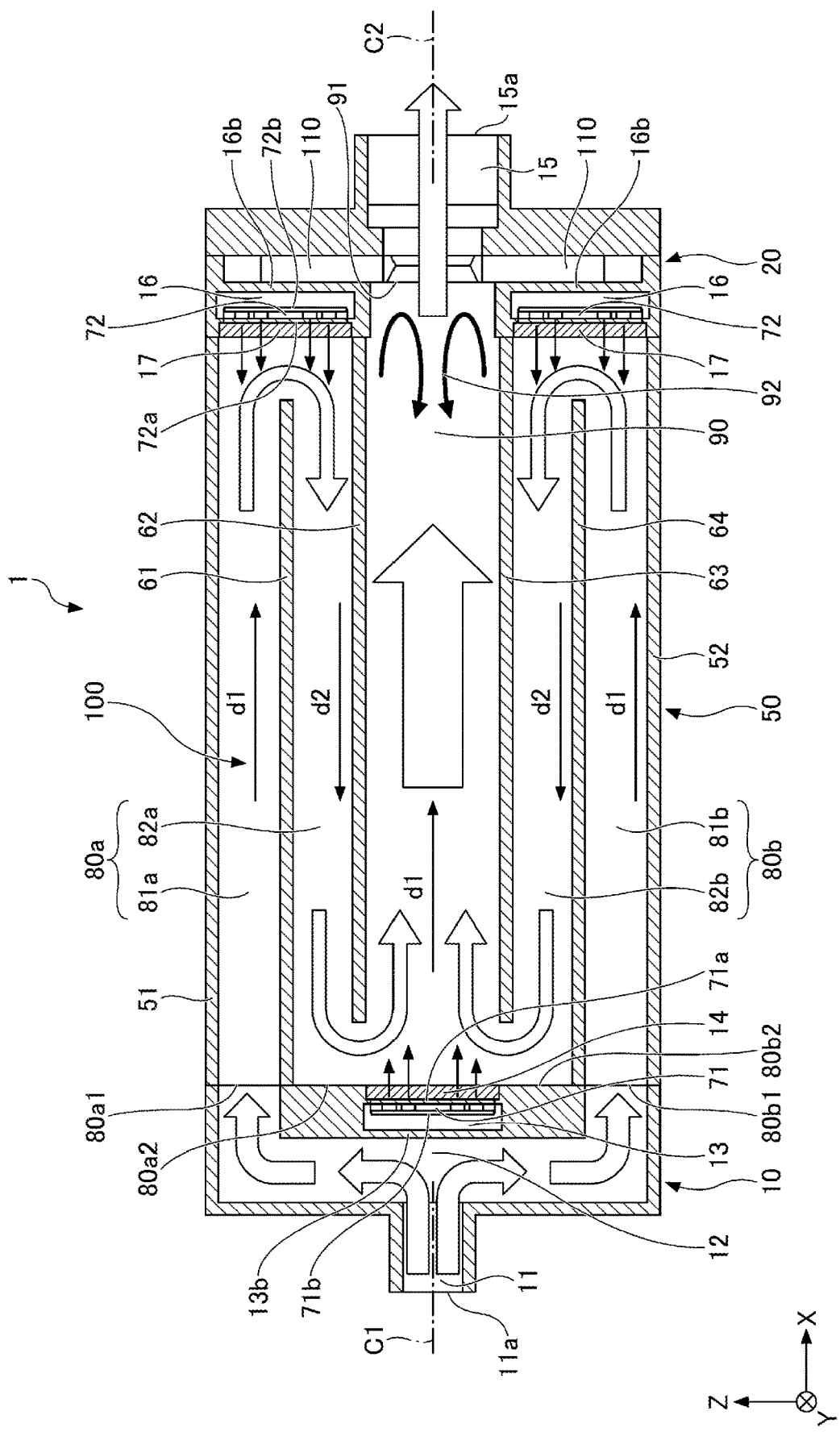
FIG. 9 schematically illustrates a cross-sectional view of the ultraviolet light fluid treatment device to explain e a first example of a fluid retention action.
Figure 10:
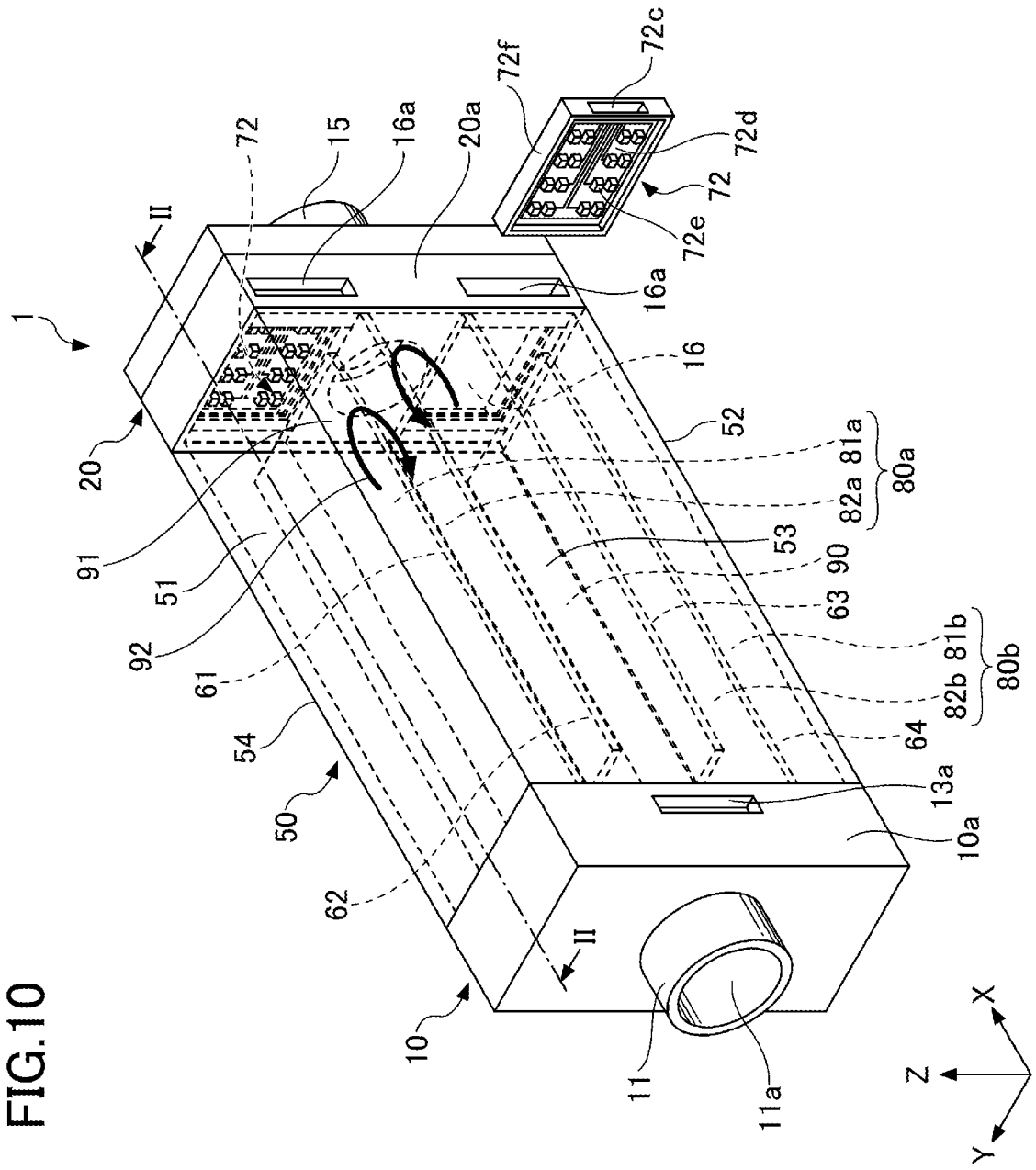
FIG. 10 schematically illustrates a perspective view of the ultraviolet light fluid treatment device to explain the first example of the fluid retention action.

A first example of the fluid retention will be described with reference to FIGS. 9 and 10. FIGS. 9 and 10 are drawings to explain the first example of the fluid retention. FIG. 9 schematically illustrates a cross-sectional view of the ultraviolet light fluid treatment device 1, and FIG. 10 schematically illustrates a perspective view of the ultraviolet light fluid treatment device 1.

An end portion 91 of the merged flow path portion 90 on the outflow portion 15 side has an opening having a cross-sectional area smaller than a cross-sectional area of the merged flow path portion 90 orthogonal to the first direction d1. As illustrated in FIGS. 9 and 10, a portion of the fluid flowing through the merged flow path portion 90 from the inflow portion 11 side toward the outflow portion 15 side in the X-axis direction is retained by hitting and then bouncing back from the end portion 91 of the merged flow path portion 90 on the outflow portion 15 side. A flow 92 indicated by the bold arrows in FIGS. 9 and 10 represents the flow of the fluid bounced back by the end portion 91.

For example, by such a flow 92, a portion of the fluid flowing through the merged flow path portion 90 is retained for a longer period of time in the vicinity of the end portion 91. It is noted that the flow 92 illustrated in FIGS. 9 and 10 is an example illustrated for convenience of explanation, and a direction and a magnitude of the flow are not limited thereto.

The first light source 71 is disposed facing the end portion 91, and thus the fluid retained in the vicinity of the end portion 91 is efficiently irradiated with ultraviolet light from the first light source 71. As a result, the integrated luminance of the ultraviolet light irradiated from the first light source 71 into the fluid retained in the vicinity of the end portion 91 is increased in accordance with the retention time, making it possible to increase the treatment effect of the ultraviolet light in the ultraviolet light fluid treatment device 1.

Second Example of Fluid Retention

Figure 11:
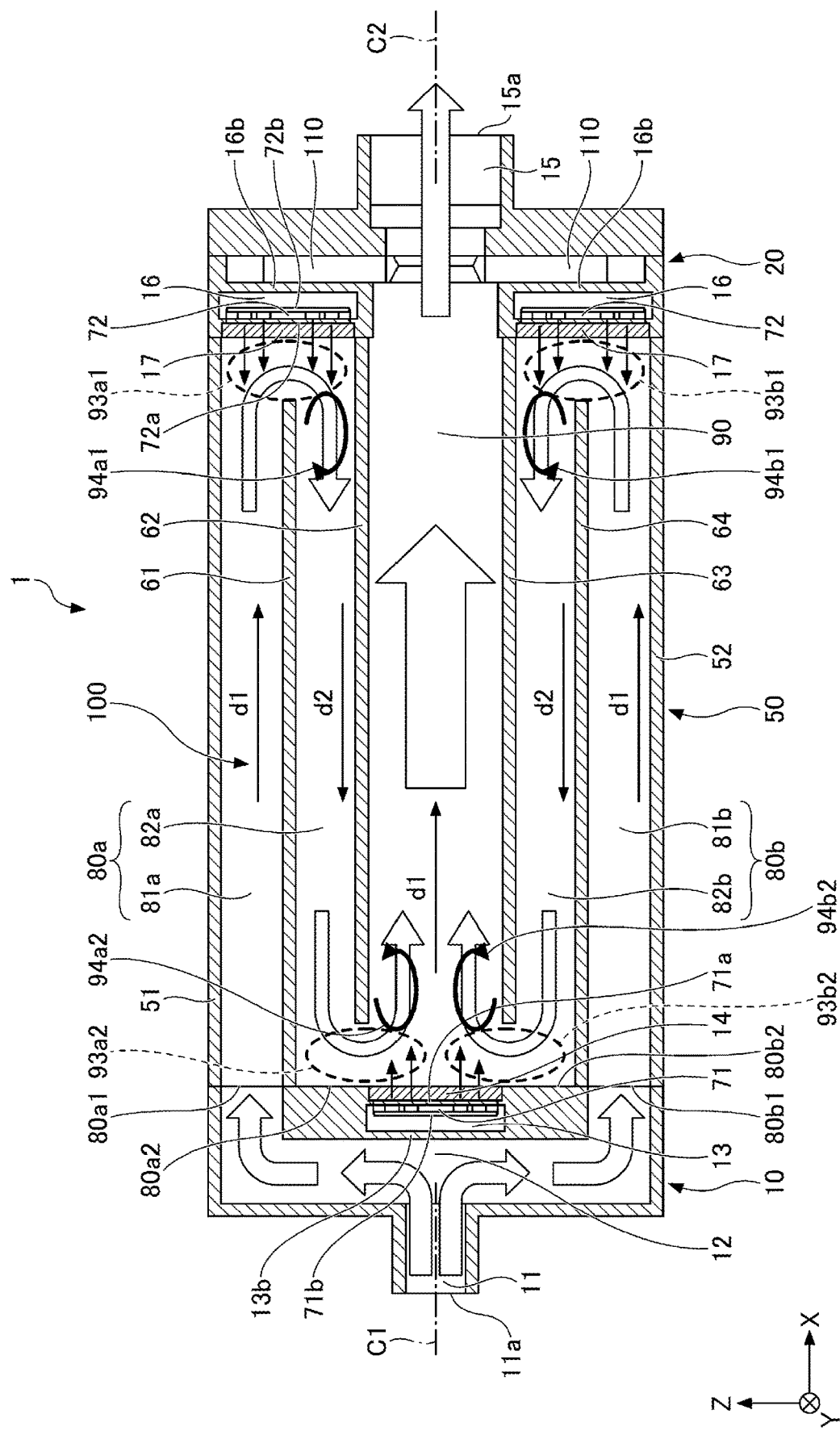
FIG. 11 schematically illustrates a cross-sectional view of the ultraviolet light fluid treatment device to explain a second example of the fluid retention action.

FIG. 11 schematically illustrates a cross-sectional view of the ultraviolet light fluid treatment device 1 to explain a second example of the fluid retention.

As illustrated in FIG. 11, a portion of the fluid flowing through the branch flow path portions 80a, 80b in the X-axis direction generates a vortex in folding back portions of the branch flow path portions 80a, 80b. Here, the term vortex refers to a swirling-like flow of fluid.

In FIG. 11, a folding back portion 93a1 indicated by a dashed line is a folding back portion from the first flow path portion 81a to the second flow path portion 82a in the branch flow path portion 80a. A vortex 94a1 indicated by the bold arrow represents a vortex generated in the vicinity of the folding back portion 93a1 in the second flow path portion 82a. The folding back portion refers to a portion in which the fluid flowing in a predetermined direction folds back in a direction opposite to the predetermined direction.

Similarly, a folding back portion 93a2 is a folding back portion from the second flow path portion 82a in the branch flow path portion 80a to the merged flow path portion 90. A vortex 94a2 represents a vortex generated in the vicinity of the folding back portion 93a2 in the merged flow path portion 90.

A folding back portion 93b1 is a folding back portion from the first flow path portion 81b to the second flow path portion 82b in the branch flow path portion 80b. A vortex 94b1 represents a vortex generated in the vicinity of the folding back portion 93b1 in the second flow path portion 82b.

A folding back portion 93b2 is a folding back portion from the second flow path portion 82b in the branch flow path portion 80b to the merged flow path portion 90. A vortex 94b2 represents a vortex generated in the vicinity of the folding back portion 93b2 in the merged flow path portion 90.

In particular, the ultraviolet light fluid treatment device 1 is configured to have a substantially rectangular shape in a cross section orthogonal to the direction of flow of the fluid, and thus a vortex is more likely to occur at each corner portion of the folding back portions 93a1, 93a2, 93b1, 93b2. Here, the term corner portion refers to a portion where surfaces intersect.

Due to the vortices such as the vortices 94a1, 94a2, 94b1, 94b2, a portion of the fluid flowing through the branch flow path portions 80a, 80b is retained for a longer period of time in the vicinities of each of the folding back portions 93a1, 93a2, 93b1, 93b2. It is noted that the vortices 94a1, 94a2, 94b1, 94b2 illustrated in FIG. 11 are examples illustrated for convenience of description, and an orientation and a magnitude of the vortices are not limited thereto.

The first light source 71 is disposed in the vicinity of each of the folding back portions 93a2, 93b2, and thus the fluid retained in the vicinity of each of the folding back portions 93a2, 93b2 is efficiently irradiated with ultraviolet light from the first light source 71. Further, the second light sources 72 are disposed in the vicinity of each of the folding back portions 93a1, 93b1, and thus the fluid retained in the vicinity of each of the folding back portions 93a1, 93b1 is efficiently irradiated with ultraviolet light from the second light sources 72.

According to the above, the integrated luminance of the ultraviolet light irradiated from the first light source 71 and the second light sources 72 into the fluid retained in the vicinity of each of the folding back portions 93a1, 93a2, 93b1, 93b2 increases in accordance with the retention time, making it possible to increase the treatment effect of the ultraviolet light in the ultraviolet light fluid treatment device 1.

Further, in a case in which the fluid is water, for example, bacteria and viruses in the water have a high specific gravity relative to water, and thus when flowing through the folding back portions 93a1, 93a2, 93b1, 93b2, the bacteria and viruses are more likely to pass near the first light source 71 and the second light sources 72 due to centrifugal force. Thus, the ultraviolet light fluid treatment device 1 can increase the integrated luminance of the ultraviolet light with respect to the bacteria and viruses in the water, and can increase the treatment effect of the ultraviolet light.

In the example illustrated in FIG. 11, the ultraviolet light fluid treatment device 1 including the plurality of branch flow path portions 80a, 80b is exemplified, but the configuration is not limited thereto. In a case in which the ultraviolet light fluid treatment device 1 includes one branch flow path portion as well, the action and effects described in the second example can be obtained.

Third Example of Fluid Retention

Figure 12:
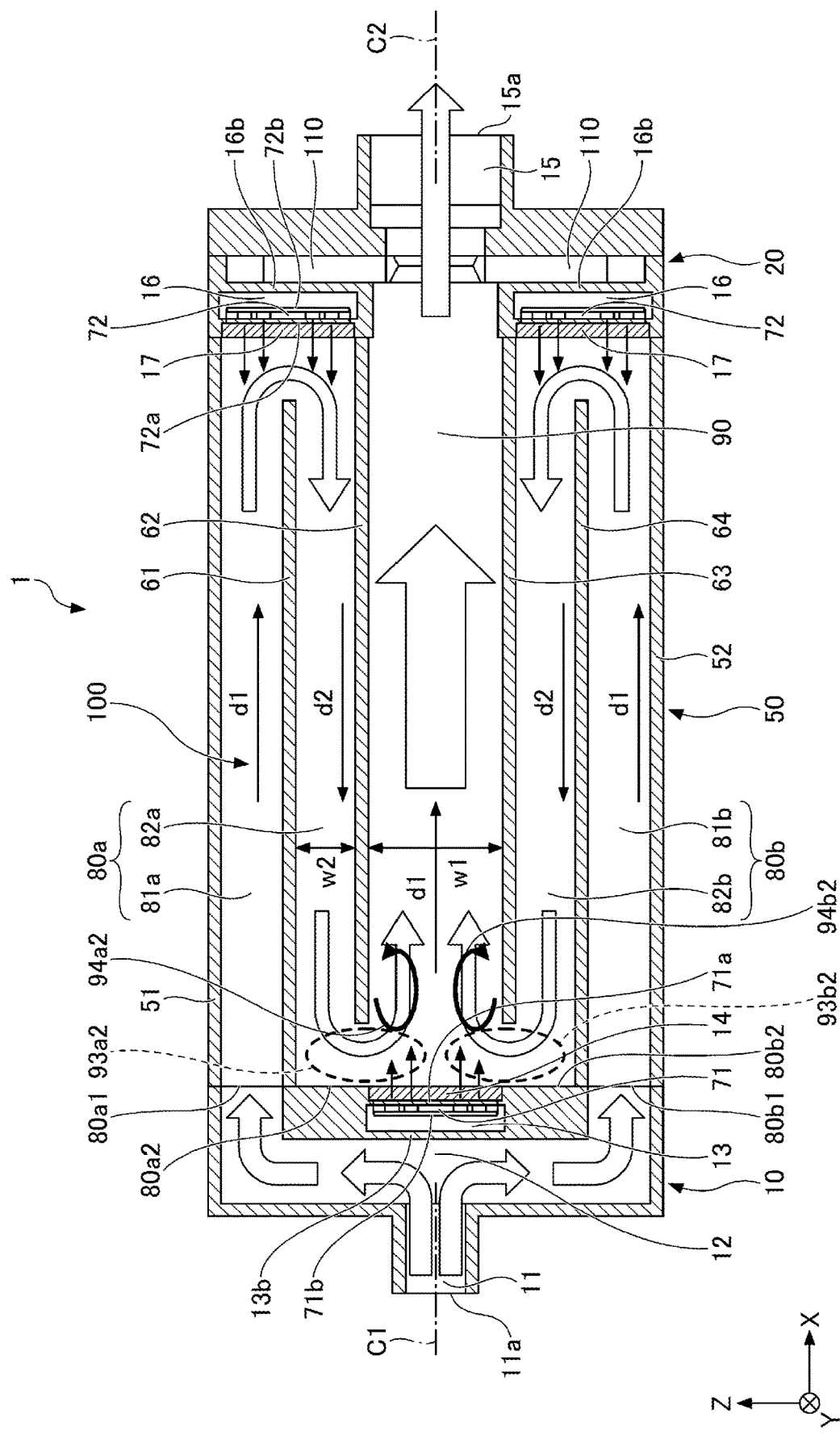
FIG. 12 schematically illustrates a cross-sectional view of the ultraviolet light fluid treatment device to explain a third example of the fluid retention action.

FIG. 12 schematically illustrates a cross-sectional view of the ultraviolet light fluid treatment device 1 to explain a third example of the action of fluid retention.

As illustrated in FIG. 12, when a width w1 of the merged flow path portion 90 is wider than a width w2 of each of the branch flow path portions 80a, 80b in a direction orthogonal to the direction of flow of the fluid, a vortex is more likely to occur. The direction orthogonal to the direction of flow of the fluid is, for example, a direction along the Y axis or a direction along the Z axis. Accordingly, in the ultraviolet light fluid treatment device 1, the width w1 along the Y axis may be wider than the width w2 along the Y axis, or the width w1 along the Z axis may be wider than the width w2 along the Z axis.

With the width w1 being wider than the width w2, a flow rate difference or a flow velocity difference is imparted between the fluid flowing through the branch flow path portion 80*a* or 80*b* and the fluid flowing through the merged flow path portion 90. Due to this flow rate difference or flow velocity difference, a vortex is more likely to occur in the vicinity of each of the folding back portions 93*a*2, 93*b*2, increasing the retention time of the fluid in the vicinity of each of the folding back portions 93*a*2, 93*b*2. In FIG. 12, the vortex 94*a*2 represents a vortex generated in the vicinity of the folding back portion 93*a*2 in the merged flow path portion 90, and the vortex 94*b*2 represents a vortex generated in the vicinity of the folding back portion 93*b*2 in the merged flow path portion 90.

The fluid retention in the vicinity of each of the folding back portions 93*a*2, 93*b*2 is similar to that described in the second example described above.

Fourth Example of Fluid Retention

Figure 13:
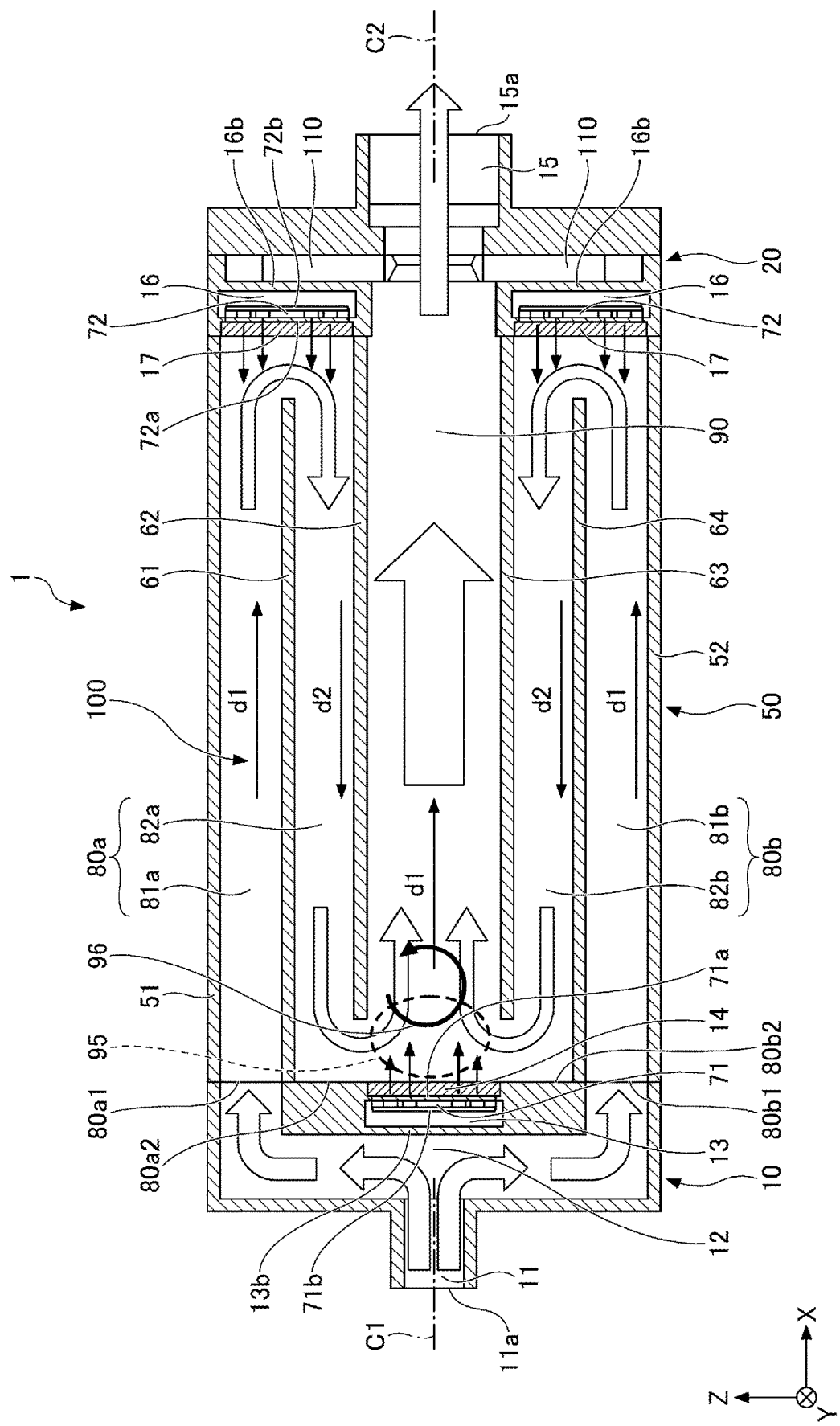
FIG. 13 schematically illustrates a cross-sectional view of the ultraviolet light fluid treatment device to explain a fourth example of the fluid retention action.

FIG. 13 schematically illustrates a cross-sectional view of the ultraviolet light fluid treatment device 1 to explain a fourth example of the fluid retention.

As illustrated in FIG. 13, when the ultraviolet light fluid treatment device 1 is positioned with the branch flow path portion 80*b* being formed vertically downward with respect to the branch flow path portion 80*a*, a vortex is more likely to occur in the vicinity of a merging portion 95 positioned on the inflow portion 11 side of the merged flow path portion 90. In FIG. 13, the Z axis is in the vertical direction.

With the branch flow path portion 80*b* being formed vertically downward with respect to the branch flow path portion 80*a*, a flow rate difference or a flow velocity difference is imparted between the fluid flowing from the branch flow path portion 80*a* into the merged flow path portion 90, and the fluid flowing from the branch flow path portion 80*b* into the merged flow path portion 90 by the action of gravity. For example, the flow rate of the fluid flowing from the branch flow path portion 80*a* into the merged flow path portion 90 increases relative to the flow rate of the fluid flowing from the branch flow path portion 80*b* into the merged flow path portion 90 to the extent of the action of gravity. Due to this flow rate difference or flow velocity difference, a vortex is more likely to occur in the vicinity of the merging portion 95 where the fluid merges, increasing the retention time of the fluid in the vicinity of the merging portion 95.

In FIG. 13, a vortex 96 represents a vortex generated in the vicinity of the merging portion 95. It is noted that the vortex 96 illustrated in FIG. 11 is an example illustrated for convenience of explanation, and an orientation and a magnitude of the vortex are not limited thereto.

The first light source 71 is disposed in the vicinity of the merging portion 95, and thus the fluid retained in the vicinity of the merging portion 95 is efficiently irradiated with ultraviolet light from the first light source 71. As a result, the integrated luminance of the ultraviolet light irradiated from the first light source 71 into the fluid retained in the vicinity of the merging portion 95 is increased in accordance with the retention time, making it possible to increase the treatment effect of the ultraviolet light in the ultraviolet light fluid treatment device 1.

Fifth Example of Fluid Retention

Figure 14:
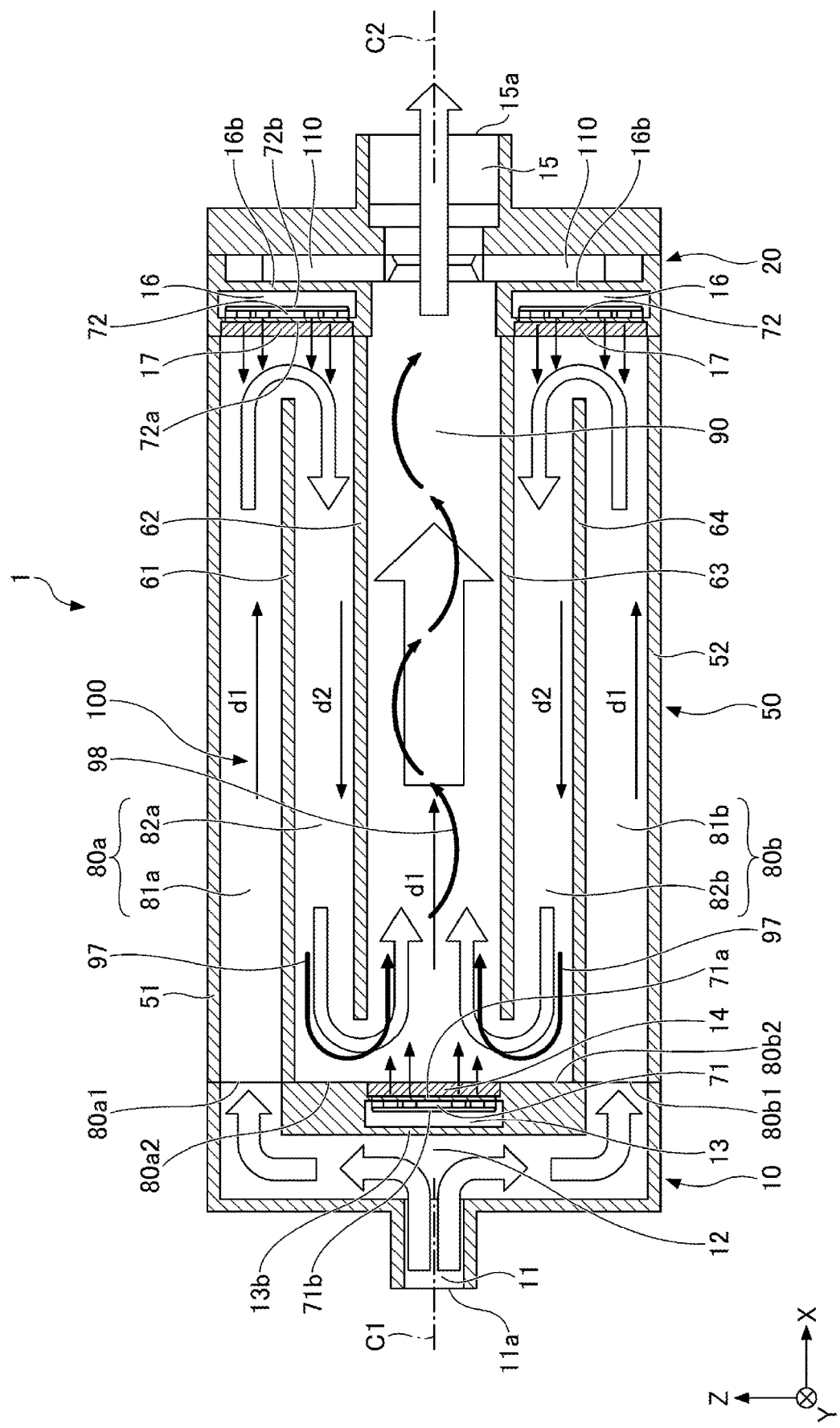
FIG. 14 schematically illustrates a cross-sectional view of the ultraviolet light fluid treatment device to explain a fifth example of the fluid retention action.

FIG. 14 schematically illustrates a cross-sectional view of the ultraviolet light fluid treatment device 1 to explain a fifth example of the fluid retention.

Similarly to the fourth example described above, in the fifth example as well, when the branch flow path portion 80*b* is formed vertically downward with respect to the branch flow path portion 80*a*, a flow rate difference or a flow velocity difference is imparted between the fluid flowing from the branch flow path portion 80*a* into the merged flow path portion 90, and the fluid flowing from the branch flow path portion 80*b* into the merged flow path portion 90. This flow rate difference or flow velocity difference causes the fluid to snake through the merged flow path portion 90, as illustrated in FIG. 14.

In FIG. 14, a flow 97 represents a flow of the fluid flowing from each of the branch flow path portions 80*a*, 80*b* into the merged flow path portion 90, and a flow 98 represents a flow of the fluid snaking through the merged flow path portion 90. For example, the flow rate of the fluid flowing from the branch flow path portion 80*a* into the merged flow path portion 90 increases relative to the flow rate of the fluid flowing from the branch flow path portion 80*b* into the merged flow path portion 90 to the extent of the action of gravity, causing the fluid immediately after the merge to flow vertically downward through the merged flow path portion 90. In other words, immediately after the merge in the merged flow path portion 90, a vector of a travel direction of the fluid from the inflow portion 11 toward the outflow portion 15 tends to tilt with respect to the X axis toward the branch flow path portion 80*a* or 80*b* side, whichever has a lower flow rate. The branch flow path portion 80*a* or 80*b* side having the lower flow rate is the vertically downward side.

The fluid flowing through the merged flow path portion 90 with the vector of the travel direction tilted to the vertically downward side is bounced back to the vertically upward side by the third partition member 63, then flows through the merged flow path portion 90 with the vector of the travel direction tilted to the vertically upward side, and subsequently is bounced back to the vertically downward side by the second partition member 62. The fluid repeats such movement, snaking through the merged flow path portion 90.

With the fluid snaking through the merged flow path 90, the distance of flow through the merged flow path portion 90 is increased, thereby conceivably increasing the time during which the fluid is retained in the merged flow path portion 90. It is noted that the flow 97 and the flow 98 illustrated in FIG. 14 are each an example illustrated for convenience of explanation, and an orientation and a magnitude of each flow are not limited thereto.

Here, the snaking of the fluid such as the flow 98 is a phenomenon that is more pronounced when the branch flow path portions 80*a*, 80*b* are separated from each other by the second partition member 62, the third partition member, and the like. In other words, the ultraviolet light fluid treatment device 1 includes the branch flow path portions 80*a*, 80*b* separated from each other, making it possible to impart a flow rate difference or a flow velocity difference to the fluid flowing through the branch flow path portions 80*a*, 80*b*, and cause the fluid to snake as in the flow 98.

For example, when the plurality of flow paths each have an annular shape in a cross section orthogonal to the direction of flow of the fluid, a multi-tube structure can be configured in which the plurality of flow paths are formed concentrically.

Nevertheless, in the case of such a multi-tube structure, because the flow paths are connected in a circumferential direction, it is less likely to impart a flow rate difference or a flow velocity difference to the fluid flowing through each of the plurality of flow paths. Accordingly, in a configuration in which each of the plurality of flow paths has an annular shape, the fluid is less likely to snake as in the flow 98.

The first light source 71 is disposed such that ultraviolet light from the first light source 71 is efficiently irradiated into the fluid flowing through the merged flow path portion 90. The fluid flowing through the merged flow path portion 90 is caused to snake, increasing the retention time and thus making it possible to increase the integrated luminance and enhance the treatment effect of the ultraviolet light in the ultraviolet light fluid treatment device 1.

Further, in a case in which the fluid is water, for example, the bacteria and viruses in the water have a high specific gravity relative to water, causing the fluid snaking through the merged flow path portion 90 to swirl and thus conceivably increase the retention time in the merged flow path portion 90. Thus, the ultraviolet light fluid treatment device 1 can increase the integrated luminance of the ultraviolet light with respect to the bacteria and viruses in the water, and can increase the treatment effect of the ultraviolet light.

Sixth Example of Fluid Retention

Figure 15:
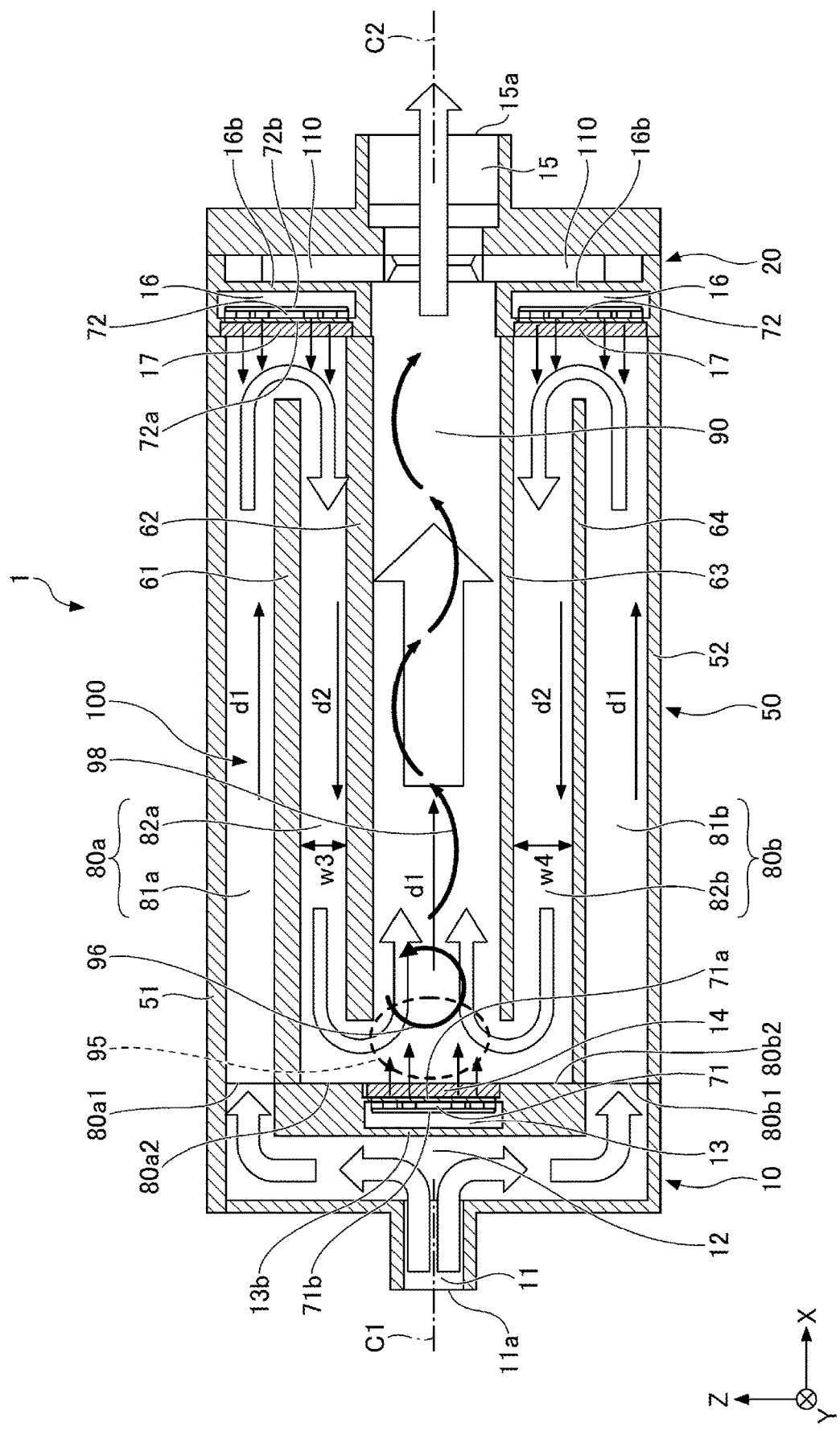
FIG. 15 schematically illustrates a cross-sectional view of the ultraviolet light fluid treatment device to explain a sixth example of the fluid retention action.

FIG. 15 schematically illustrates a cross-sectional view of the ultraviolet light fluid treatment device 1 to explain a sixth example of the fluid retention.

In the sixth example, a width of at least one of the plurality of branch flow path portions in the direction orthogonal to the direction of flow of the fluid differs from a width of the other branch flow path portions in the direction orthogonal to the direction of flow of the fluid. In the example illustrated in FIG. 15, in the direction orthogonal to the direction of flow of the fluid, a width w3 of the branch flow path portion 80a and a width w4 of the branch flow path portion 80b differ. With the width w3 of the branch flow path portion 80a and the width w4 of the branch flow path portion 80b differing in the direction orthogonal to the direction of flow of the fluid, vortices and snaking are more likely to occur.

The direction orthogonal to the direction of flow of the fluid is, for example, a direction along the Y axis or a direction along the Z axis. Accordingly, in the ultraviolet light fluid treatment device 1, the width w3 along the Y axis and the width w4 along the Y axis may differ, or the width w3 along the Z axis and the width w4 along the Z axis may differ. In the sixth example, an installation orientation of the ultraviolet light fluid treatment device 1 is not particularly limited. This is also true for the fluid retention action, with the exception of the fourth example and the fifth example.

FIG. 15 illustrates a configuration in which the width w3 of the second flow path portion 82a in the branch flow path portion 80a is narrower than the width w4 of the second flow path portion 82b in the branch flow path portion 80b, thereby making the two different from each other, but the configuration is not limited thereto. For example, the width w3 of the second flow path portion 82a may be wider than the width w4 of the second flow path portion 82b, thereby making the two different from each other. Further, in the direction orthogonal to the direction of flow of the fluid, a width of the first flow path portion 81a in the branch flow path portion 80a and a width of the first flow path portion 81b in the branch flow path portion 80b may be different from each other. In FIG. 15, the width of the first flow path portion 81a and the width of the second flow path portion 82a in the direction orthogonal to the direction of flow of the fluid are the same, but may be different. Further, the width of the first flow path portion 81b and the width of the second flow path portion 82b are the same, but may be different.

With the width w3 and the width w4 being different, a flow rate difference or a flow velocity difference is imparted between the fluid flowing from the branch flow path portion 80a into the merged flow path portion 90, and the fluid flowing from the branch flow path portion 80b into the merged flow path portion 90. For example, when the width w3 is narrower than the width w4, the flow rate of the fluid flowing from the branch flow path portion 80a into the merged flow path portion 90 decreases relative to the flow rate of the fluid flowing from the branch flow path portion 80b into the merged flow path portion 90. Due to this flow rate difference or flow velocity difference, a vortex is more likely to occur in the vicinity of the merging portion 95 where the fluid merges, increasing the retention time of the fluid in the vicinity of the merging portion 95. Further, the fluid snakes through the merged flow path portion 90 due to the flow rate difference or the flow velocity difference, thereby increasing the retention time of the fluid in the merged flow path portion 90.

The action and effects of a vortex such as the vortex 96 in the merging portion 95 are similar to those described in the fourth example described above. Further, the action and effects resulting from the snaking of the flow 98 and the like in the fluid flowing through the merged flow path portion 90 are similar to those described in the fifth example described above.

It is noted that, in the above embodiments, the two branch flow path portions 80a, 80b are exemplified as the plurality of branch flow path portions, but the configuration is not limited thereto. In a case in which the ultraviolet light fluid treatment device 1 includes three or more branch flow path portions, as long as a length of at least one of the three or more branch flow path portions in the direction orthogonal to the direction of flow of the fluid differs from a length of the other branch flow path portions in the direction orthogonal to the direction of flow of the fluid, the action and effects described in the sixth example can be obtained.

Seventh Example of Fluid Retention

Figure 16:
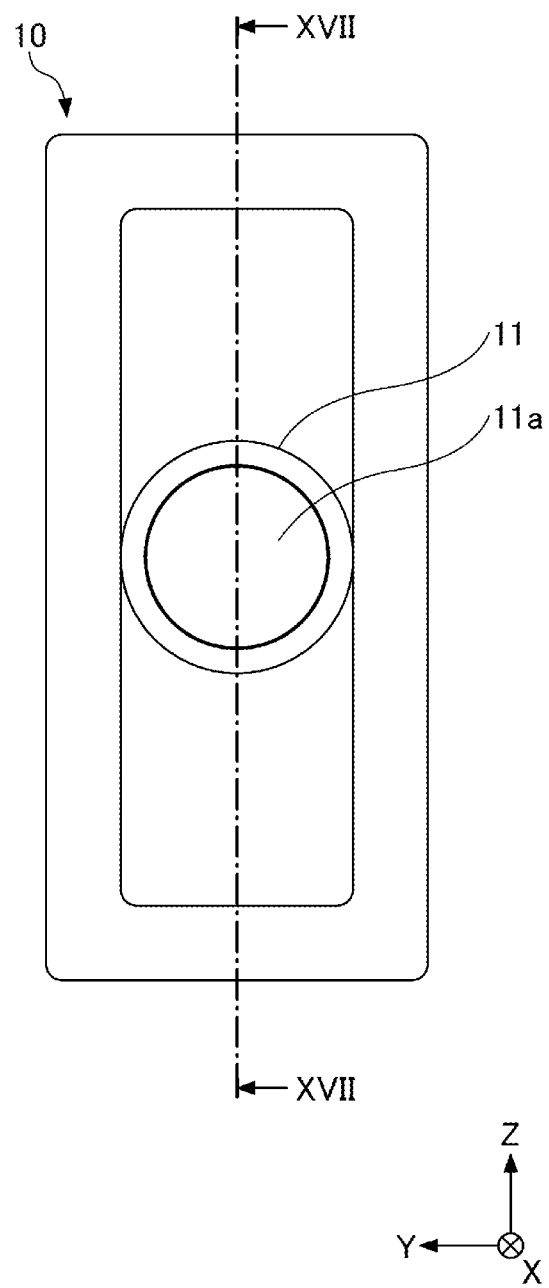
FIG. 16 schematically illustrates a lateral side view of the ultraviolet light fluid treatment device to explain a seventh example of the fluid retention action, as viewed from an inflow portion side.
Figure 17:
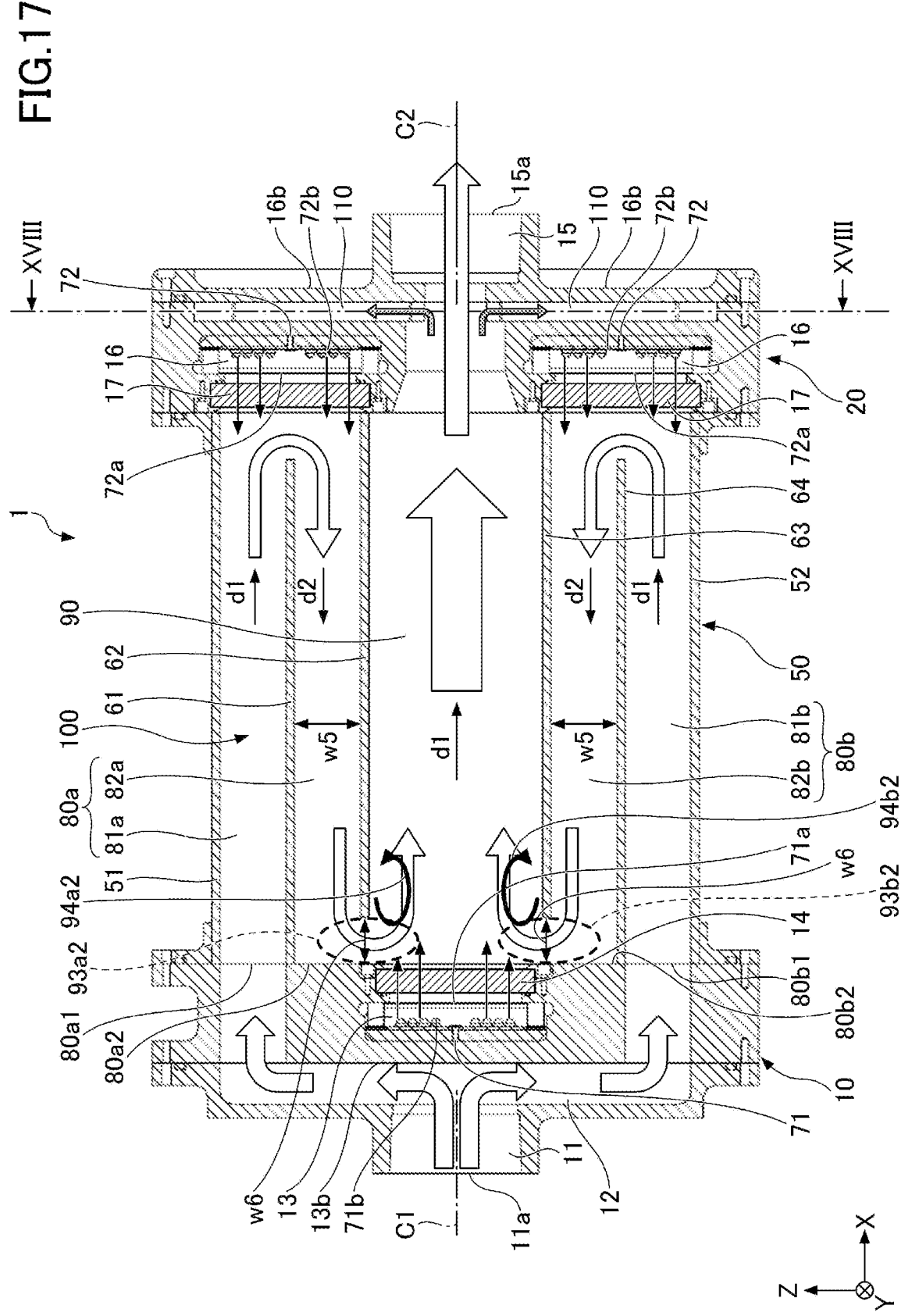
FIG. 17 schematically illustrates a cross-sectional view of the ultraviolet light fluid treatment device taken along line XVII-XVII in FIG. 16.
Figure 18:
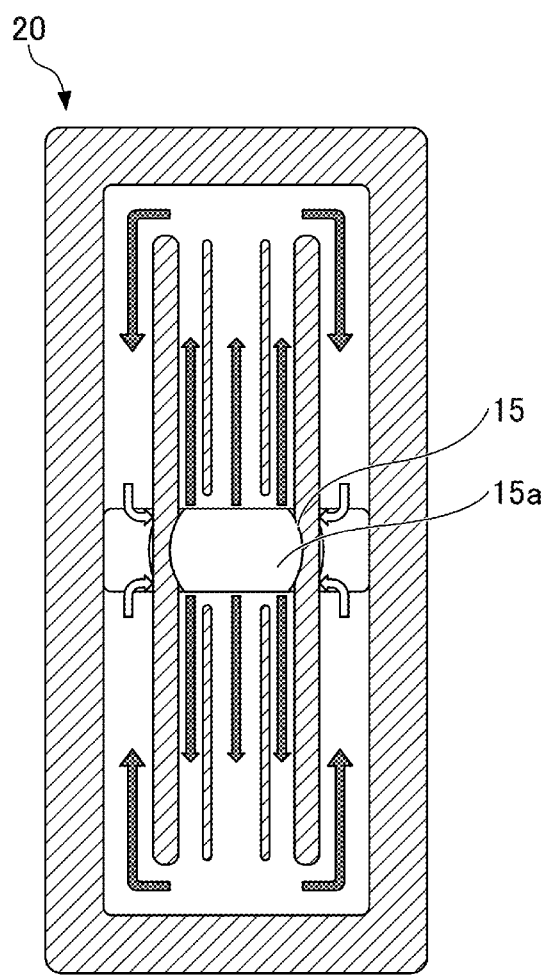
FIG. 18 schematically illustrates a cross-sectional view of the ultraviolet light fluid treatment device taken along line XVIII-XVIII in FIG. 17.

FIGS. 16 to 18 illustrate the ultraviolet light fluid treatment device 1 to explain a seventh example of the fluid retention. FIG. 16 schematically illustrates a lateral side view from the inflow portion 11 side, FIG. 17 schematically illustrates a cross-sectional view taken along line XVII-XVII in FIG. 16, and FIG. 18 schematically illustrates a cross-sectional view taken along line XVIII-XVIII in FIG. 17.

In FIGS. 17 to 18, white arrows indicate a flow of a portion of the fluid of the primary flow that flows through the inflow portion 11, into the ultraviolet light fluid treatment device 1, through the outflow portion 15, and out from the ultraviolet light fluid treatment device 1. Further, in FIGS. 16 to 18, the dot-hatched arrows indicate the flow of, among the fluid flowing through the ultraviolet light fluid treatment device 1, the fluid used to cool the second light sources 72.

As illustrated in FIG. 17, when a width w5 of the branch flow path portion 80a in the direction orthogonal to the extending direction of the branch flow path portions 80a, 80b and a width w6 of the folding back portions 93a2, 93b2 in a direction following the extending direction of the branch flow path portions 80a, 80b differ from each other, a vortex is more likely to occur.

The extending direction of the branch flow path portions 80a, 80b is, for example, a direction along the X axis. The direction orthogonal to the extending direction of the branch flow path portions 80a, 80b is, for example, a direction along the Y axis, or a direction along the Z axis. Accordingly, in the ultraviolet light fluid treatment device 1, the width w5 along the Y axis and the width w6 along the X axis may be different, or the width w5 along the Z axis and the width w6 along the X axis may be different.

With the width w5 and the width w6 differing from each other, a flow rate difference or a flow velocity difference is imparted between the fluid flowing through the branch flow path portion 80a, 80b and the fluid flowing through the folding back portions 93a2, 93b2. Due to this flow rate difference or flow velocity difference, a vortex is more likely to occur in the vicinity of each of the folding back portions 93a2, 93b2, increasing the retention time of the fluid in the vicinity of each of the folding back portions 93a2, 93b2.

The action and effects of the fluid retention in the vicinity of each of the folding back portions 93a2, 93b2 are similar to those described in the second example described above. Further, in the folding back portions 93a1, 93a2 as well, similar action and effects of fluid retention can be obtained.

In the ultraviolet light fluid treatment device 1 illustrated in FIG. 17, a length in the X-axis direction of each of the first flow path portions 81a, 81b and the second flow path portions 82a, 82b is 200 mm, for example. Further, the width of each of the first flow path portions 81a, 81b and the second flow path portions 82a, 82b in the Z-axis direction is, for example, 24 mm. The width of each of the first flow path portions 81a, 81b and the second flow path portions 82a, 82b in the Y-axis direction is, for example, 60 mm. The flow rate of the fluid flowing through the ultraviolet light fluid treatment device 1 illustrated in FIG. 17 is preferably 3 $m^3/h$ or higher. By ensuring a flow rate of 3 $m^3/h$ or higher, it is possible to suppress the presence of residual air bubbles in the interior of the ultraviolet light fluid treatment device 1. This suppresses a reduction in integrated luminance caused by the ultraviolet light irradiated from the first light source 71 and the second light sources 72 being reflected or scattered by air bubbles, making it possible to increase the integrated luminance of the ultraviolet light and increase the treatment effect of the ultraviolet light in the ultraviolet light fluid treatment device 1. Further, in the ultraviolet light fluid treatment device 1, a decrease in heat transfer efficiency due to air bubbles entering the downstream flow path portion 110 can be suppressed, and a decrease in cooling efficiency of the second light sources 72 due to the fluid flowing through the downstream flow path portion 110 can be suppressed. It is noted that the dimensions of the ultraviolet light fluid treatment device 1 and the flow rate of the fluid are not limited to the above.

The embodiments of the present invention have been described above with reference to specific examples. However, the present invention is not limited to these specific examples. All aspects that can be practiced by a person skilled in the art modifying the design as appropriate based on the above-described embodiments of the present invention are also included in the scope of the present invention, as long as they encompass the spirit of the present invention. In addition, in the spirit of the present invention, a person skilled in the art can conceive of various alteration examples and modifications, and those alteration examples and modifications will also fall within the scope of the present invention.

The invention claimed is:

1. An ultraviolet light fluid treatment device comprising:
   an inlet;
   an outlet;
   a primary conduit connecting the inlet and the outlet;
   a secondary conduit branching off the primary conduit at a first location of the primary conduit and merging with the primary conduit at a second location of the primary conduit; and
   a light source disposed between the primary conduit and the secondary conduit and configured to emit ultraviolet light, with which a region in the primary conduit is irradiated,
   a cross-sectional area in the primary conduit orthogonal to a first flow direction of a fluid in the primary conduit at the first location being greater than a cross-sectional area in the secondary conduit orthogonal to a second flow direction of the fluid in the secondary conduit at the first location.

2. The ultraviolet light fluid treatment device according to claim 1, wherein the second location is downstream with respect to the first location in the first flow direction.

3. The ultraviolet light fluid treatment device according to claim 1, wherein the first location is upstream with respect to the region in the first flow direction.

4. The ultraviolet light fluid treatment device according to claim 1, wherein the first location is downstream with respect to the region in the first flow direction.

5. The ultraviolet light fluid treatment device according to claim 1, wherein the second location is upstream with respect to the region in the first flow direction.

6. The ultraviolet light fluid treatment device according to claim 1, wherein the second location is downstream with respect to the region in the first flow direction.

7. The ultraviolet light fluid treatment device according to claim 1, wherein the cross-sectional area in the primary conduit at the first location is greater than a cross sectional-area in the primary conduit orthogonal to the first flow direction at the second location.

8. The ultraviolet light fluid treatment device according to claim 1, wherein a region in the secondary conduit is also irradiated with the ultraviolet light.

9. The ultraviolet light fluid treatment device according to claim 1, further comprising:
   a second light source disposed between the primary conduit and the secondary conduit and configured to emit ultraviolet light, with which a second region in the primary conduit is irradiated.

10. The ultraviolet light fluid treatment device according to claim 1, wherein the light source has a surface from which the ultraviolet light is emitted, the light source including on the surface an elastic member, which urges the light source toward the secondary conduit.

11. An ultraviolet light fluid treatment device comprising:
    an inlet;
    an outlet;
    a primary conduit connecting the inlet and the outlet, the primary conduit forming first and second flow paths that are split at a first location and merge at a second location downstream with respect to the first location along a flow of a fluid in the primary conduit, each of the first and second flow paths being formed such that the fluid flows in a first direction from the inlet to the outlet, and then in a second direction opposite to the first direction;
    a first light source configured to emit ultraviolet light, with which the first flow path is irradiated; and
    a second light source configured to emit ultraviolet light, with which the second flow path is irradiated.

12. The ultraviolet light fluid treatment device according to claim 11, wherein the primary conduit is configured such that the fluid flows in the first direction after the first and second flow paths merge.

13. The ultraviolet light fluid treatment device according to claim 11, wherein
    the first light source is disposed at a third location of the primary conduit, at which the flow of the fluid in the first flow path changes from the first direction to the second direction, and the second light source is disposed at a fourth location of the primary conduit, at which the flow of the fluid in the second flow path changes from the first direction to the second direction.

14. The ultraviolet light fluid treatment device according to claim 11, further comprising:
a third light source configured to emit ultraviolet light, with which a merged flow path of the first and second flow paths at the second location is irradiated.

15. The ultraviolet light fluid treatment device according to claim 11, wherein the second flow path is below the first flow path in a gravity direction.

16. The ultraviolet light fluid treatment device according to claim 11, wherein a width of the first flow path is less than a width of a merged flow path of the first and second flow paths.

17. The ultraviolet light fluid treatment device according to claim 11, wherein a width of the first flow path is less than a width of the second flow path.

18. The ultraviolet light fluid treatment device according to claim 11, further comprising:
a secondary conduit branching off the primary conduit at a fifth location of the primary conduit downstream with respect to the second location along the flow of the fluid, and merging with the primary conduit at a sixth location of the primary conduit downstream with respect to the fifth location along the flow of the fluid.

19. The ultraviolet light fluid treatment device according to claim 18, wherein
the first light source is disposed between the first flow path and the secondary conduit, and
the second light source is disposed between the second flow path and the secondary conduit.

20. The ultraviolet light fluid treatment device according to claim 18, wherein a cross-sectional area in the primary conduit orthogonal to the first direction at the fifth location is greater than a cross-sectional area in the secondary conduit orthogonal to a flow direction of the fluid in the secondary conduit at the fifth location.

* * * * *